(12) United States Patent
Krueger

(10) Patent No.: US 9,370,302 B2
(45) Date of Patent: Jun. 21, 2016

(54) SYSTEM AND METHOD FOR THE MEASUREMENT OF VESTIBULO-OCULAR REFLEX TO IMPROVE HUMAN PERFORMANCE IN AN OCCUPATIONAL ENVIRONMENT

(71) Applicant: Wesley W. O. Krueger, San Antonio, TX (US)

(72) Inventor: Wesley W. O. Krueger, San Antonio, TX (US)

(*) Notice: Subject to any disclaimer, the term of this patent is extended or adjusted under 35 U.S.C. 154(b) by 171 days.

(21) Appl. No.: 14/326,335

(22) Filed: Jul. 8, 2014

(65) Prior Publication Data
US 2016/0007849 A1    Jan. 14, 2016

(51) Int. Cl.
| | | |
|---|---|---|
| G06F 3/01 | (2006.01) | |
| A61B 3/11 | (2006.01) | |
| A61B 3/113 | (2006.01) | |
| A61B 5/0496 | (2006.01) | |
| A61B 5/05 | (2006.01) | |
| A61B 5/11 | (2006.01) | |
| A61B 5/00 | (2006.01) | |

(52) U.S. Cl.
CPC .............. *A61B 3/113* (2013.01); *A61B 5/0002* (2013.01); *A61B 5/0496* (2013.01); *A61B 5/05* (2013.01); *A61B 5/1128* (2013.01); *A61B 5/6803* (2013.01); *A61B 5/7257* (2013.01); *A61B 3/112* (2013.01); *G06F 3/012* (2013.01); *G06F 3/013* (2013.01)

(58) Field of Classification Search
CPC .......... A61B 3/00–3/18; A61B 5/0496; A61B 5/1128; A61B 5/4863; A61B 5/6803; A61B 5/7257; A61B 5/002; G06F 3/012; G06F 3/013; G06F 19/3418
See application file for complete search history.

(56) References Cited

U.S. PATENT DOCUMENTS

| | | | |
|---|---|---|---|
| 4,817,633 A | 4/1989 | McStravick et al. | |
| 5,550,601 A | 8/1996 | Donaldson | |
| 5,555,895 A | 9/1996 | Ulmer et al. | |
| 5,838,420 A | 11/1998 | MacGregor Donaldson | |
| 5,919,149 A | 7/1999 | Allum | |
| 5,942,954 A | 8/1999 | Galiana et al. | |
| 5,953,102 A | 9/1999 | Berry | |
| 6,796,947 B2 | 9/2004 | Watt et al. | |
| 7,651,224 B2 | 1/2010 | Wood et al. | |

(Continued)

FOREIGN PATENT DOCUMENTS

WO   WO 2013117727   8/2013

OTHER PUBLICATIONS

Allison et al. Combined Head and Eye Tracking System for Dynamic Testing of the Vestibular System. IEEE Transactions on Biometical Engineering, vol. 43 No. 11 Nov. 1996. (USA).

*Primary Examiner* — Larry Sternbane
(74) *Attorney, Agent, or Firm* — Kilpatrick Townsend & Stockton LLP

(57) ABSTRACT

A portable eye reflex measuring device for use in an ambulatory occupational environment is disclosed. The eye reflex measuring device compares data from an eye movement detector with data from a head movement detector at a frequency or frequencies in the range of 0.01 Hertz to 15 Hertz to determine eye response to head movement. The gain and phase of the eye response is calculated using a Fourier transform. The device includes a central processing unit for receiving the eye movement data, for receiving the head movement data, and for calculating the Fourier transform. Typical human physiological conditions that can be measured can include vestibulo-ocular reflex, dynamic visual acuity, dynamic visual stability, or retinal image stability.

19 Claims, 4 Drawing Sheets

(56) References Cited

U.S. PATENT DOCUMENTS

| | | |
|---|---|---|
| 7,727,162 B2 | 6/2010 | Peterka |
| 8,253,814 B2 | 8/2012 | Zhang et al. |
| 8,285,416 B2 | 10/2012 | Cho et al. |
| 8,510,166 B2 | 8/2013 | Neven |
| 8,529,463 B2 | 9/2013 | Della Santina et al. |
| 2002/0118339 A1 | 8/2002 | Lowe |
| 2010/0036289 A1 | 2/2010 | White et al. |
| 2015/0212576 A1* | 7/2015 | Ambrus ................ G06F 3/013 345/156 |

* cited by examiner

SYSTEM AND METHOD FOR THE MEASUREMENT OF VESTIBULO-OCULAR REFLEX TO IMPROVE HUMAN PERFORMANCE IN AN OCCUPATIONAL ENVIRONMENT

BACKGROUND

The present invention relates to systems and methods for the measurement and improvement of human eye response to orientation information that comes from the vestibular system in the inner ear. Terms used to describe this ocular response include the vestibulo-ocular reflex or vestibular ocular reflex (both referred to as the VOR). Other terms used to describe this ocular response include dynamic visual acuity, kinetic visual acuity, dynamic visual stability, and retinal image stability. More specifically, in one embodiment, the present invention comprises a portable, battery-powered device for measuring and improving the VOR and/or other physiologic eye responses. The portable device could be head-worn, otherwise user attachable, or hand-held. The device could be used to (a) measure the ocular responses that relate to and predict the performance of the user when performing an activity and/or to (b) provide a means for improving or enhancing the VOR or other eye responses associated with head movement of a subject.

It is desirable to have a device that could be worn anywhere for ambulatory testing in a non-clinical or non-laboratory environment. The device should be lightweight, portable, ergonomic, and aesthetically pleasing compared to the prior art hard wired, laboratory and clinical technologies, typically affixed to a desktop computer system or similar non-portable device. One example of a laboratory technology to be eliminated is an external pulsed magnetic field, which was used by Allison et al (IEEE Transactions on Biomedical Engineering, November 1996). Such a magnetic field would make it impossible to use the device outside the laboratory. The desired device should track eye gaze and other movement related activity of the eyes. The device should measure the VOR or another type of human eye response to changes in head orientation.

1. DEFINITIONS

The definitions in the following paragraphs apply to the terminology used in describing the content and embodiments in this disclosure as well as the related claims.

The vestibular system is the complex system of the inner ear that helps provide human balance. The vestibular system consists of the saccule, utricle and semicircular canals. The vestibular system is also called the vestibular apparatus and is often referred to as being part of the labyrinth.

The saccule and utricle collectively comprise what is referred to as the otolith organs. The otolith organs detect position of the head relative to gravity and linear acceleration according to their orientation, when motion occurs in a straight line, to orientate the body in space. The saccule is oriented vertically and registers accelerations in the vertical plane, including the force due to gravity. Therefore, it detects linear motion in the vertical plane, such as ascending or descending in an elevator. It can also provide information about tilting of the head in the vertical plane. When the head moves vertically, the sensor cells of the saccule are disturbed and the neurons connected to them begin transmitting impulses to the brain. These impulses travel along the vestibular portion of the eighth cranial nerve to the vestibular nuclei in the brainstem. The utricle is largely positioned horizontally in the inner ear. The utricle registers accelerations in the horizontal plane of the head, as well as tilt information. Therefore, linear motion in the horizontal plane is sensed, such as moving horizontally in a vehicle. Acute injuries to the utricle are known to cause a subjective tilt of the world. Any orientation of the head causes a combination of stimulation to the utricles and saccules of the two ears. The brain interprets head orientation by comparing these inputs to each other and to other input from the eyes and stretch receptors in the neck, thereby detecting whether only the head is tilted or the entire body is tipping.

The semicircular canals are comprised of three fluid-filled bony channels in the inner ear. The semicircular canals are arranged at right angles to each other and are referred to as the superior (or anterior) semicircular canal, the horizontal (or lateral) semicircular canal and the posterior semicircular canal. Collectively the semicircular canals are referred to as the kinetic labyrinth, because they respond to rotation and angular acceleration. These semicircular canals or channels communicate, by a neural network, with the brain and visual system to provide orientation and balance. Therefore, as a unit, the saccule, utricle and semicircular canals are involved with balance and maintenance of a stable visual image.

Vestibulo-ocular terminology is often spelled interchangeably with vestibular ocular and both refer to the relationship of the vestibular (e.g. inner ear) system as it relates to the ocular system (e.g. vision) with respect to the reflex response with head movement including gain, phase, and symmetry at various frequencies.

VOR is an involuntary movement of the eyes in response to rotational movements of the head that is detected by the inner ear balance system. The VOR stabilizes the visual image on the back of the eye (retina) during head movement by producing an eye movement in the direction opposite to head movement, thus preserving the image on the center of the visual field. A simplistic view of the VOR involves a 3-neuron arc that consists of the vestibular ganglion, vestibular nuclei, and oculomotor nuclei. When the head moves, the VOR responds with an eye movement that is equal in magnitude but opposite in direction. Head movements, rotational and translational, stimulate the VOR. With a rotational movement, the head moves relative to the body. Examples of this include turning the head back and forth, nodding, and bringing the ear in contact with the shoulder. Translational movements occur when the entire body, including the head, is moved in tandem. Translational movements may occur when an individual stands on a moving sidewalk. Thus, rotational VOR responds to angular motion of the head and results from stimulation of the semicircular canals, whereas translational VOR responds to linear motion of the head and results from stimulation of the otolithic organs. Some head movements may involve a combination of both translational VOR and rotational VOR. The VOR is a reflex that acts at short latency to generate eye movements that compensate for head rotations in order to preserve clear vision during locomotion. The VOR is the most accessible gauge of vestibular function. Evaluating the VOR requires application of a vestibular stimulus and measurement of the resulting eye movements. For example, when the head moves to the right, the eyes move to the left, and vice versa. The VOR normally serves to stabilize gaze in space during head movements by generating equal and opposite compensatory eye movements. The VOR has both rotational and translational aspects. When the head rotates about any axis (horizontal, vertical, or torsional) distant visual images are stabilized by rotating the eyes about the same axis, but in the opposite direction. When the head translates, for example during walking, the visual fixation point is maintained by rotating gaze direction in the opposite direction, by an amount that depends on distance. Eye movements generated by the human VOR system are intended to stabilize the image on the retina during brief, non-sustained head movements. In order to see the surrounding world clearly the retinal images must remain stable, within certain margins. Stability is affected, however, by the continuous movements of the head, which may cause motion blur. In order to prevent motion blur, head movements are counter-balanced by compensatory eye movements. These are mediated by two reflexes, the VOR, which senses head rotations in the labyrinth, and the optokinetic reflex (OKR), which directly senses visual image motion.

A saccade is a fast movement of an eye, head or other part of the body or of a device. It can also be a fast shift in frequency of an emitted signal or other quick change. Saccades are quick, simultaneous movements of both eyes in the same direction. Humans do not look at a scene in fixed steadiness, the eyes move around, locating interesting parts of the scene and building up a mental, three-dimensional 'map' corresponding to the scene. When scanning the scene in front of you or reading these words right now, your eyes make jerky saccadic movements and your eyes stop several times, moving very quickly between each stop. We cannot consciously control the speed of movement during each saccade; the eyes move as fast as they can. One reason for the saccadic movement of the human eye is that the central part of the retina (known as the fovea) plays a critical role in resolving objects. By moving the eye so that small parts of a scene can be sensed with greater resolution, body resources can be used more efficiently.

Nystagmus is a description of abnormal involuntary or uncontrollable eye movement, characterized by jumping (or back and forth) movement of the eyes, which results in reduced or limited vision. It is often called "dancing eyes". Nystagmus can occur in three directions: (1) side-to-side movements (horizontal nystagmus), (2) up and down movements (vertical nystagmus), or (3) rotation of the eyes as seen when observing the front of the face (rotary or torsional nystagmus).

The Visual acuity (VA) refers to acuteness or clearness of vision, which is dependent on optical and neural factors, i.e., (i) the sharpness of the retinal focus within the eye, (ii) the intactness and functioning of the retina, and (iii) the sensitivity of the interpretative faculty of the brain. A Snellen chart (eye chart that uses block letters arranged in rows of various sizes) is frequently used for visual acuity testing and measures the resolving power of the eye, particularly with its ability to distinguish letters and numbers at a given distance as well as the sharpness or clearness of vision.

The dynamic visual acuity (DVA) can be used interchangeably with kinetic visual acuity as they both have the same meaning. In this document, DVA will be used to assess impairments in a person's ability to perceive objects accurately while actively moving the head, or the ability to track a moving object. It is an eye stabilization measurement while the head is in motion. In normal individuals, losses in visual acuity are minimized during head movements by the VOR system that maintains the direction of gaze on an external target by driving the eyes in the opposite direction of the head movement. When the VOR system is impaired, visual acuity degrades during head movements. The DVA is an impairment test that quantifies the impact of the VOR system pathology on a user's ability to maintain visual acuity while moving. Information provided by the DVA is complementary to and not a substitute for physiological tests of the VOR system. The DVA quantifies the combined influences of the underlying vestibulo-ocular reflex pathology and the patient's adaptive response to pathology. DVA testing is sometimes obtained for those persons suspected of having an inner ear abnormality. Abnormalities usually correlate with oscillopsia (a visual disturbance in which objects in the visual field appear to oscillate or jump while walking or moving). With the current standing DVA testing worsening of visual acuity by at least three lines on a visual acuity chart (e.g., Snellen chart or Rosenbaum card) during head turning from side to side at 1 Hz or more is reported as being abnormal. In normal individuals, losses in visual acuity are minimized during head movements by the vestibulo-ocular reflex (VOR) system that maintains the direction of gaze on an external target by driving the eyes in the opposite direction of the head movement When the VOR system is impaired, visual acuity degrades during head movements. Patients with VOR deficits can improve their dynamic acuity by performing rapid "catch-up" saccadic eye movements and/or with predictive saccades.

Dynamic visual stability (DVS) and retinal image stability (RIS) can be used interchangeably. In this document, DVS will be used to describe the ability to visualize objects accurately while actively moving the head. When the eye moves over the visual scene, the image of the world moves about on the retina, yet the world or image observed is perceive as being stable. DVS enables a person to prevent perceptual blurring when the body moves actively. The goal of oculomotor compensation is not retinal image stabilization, but rather controlled retinal image motion adjusted to be optimal for visual processing over the full range of natural motions of the body or with head movement. Although we perceive a stable visual world, the visual input to the retina is never stationary. Eye movements continually displace the retinal projection of the scene, even when we attempt to maintain steady fixation. Our visual system actively perceives the world by pointing the fovea, the area of the retina where resolution is best, towards a single part of the scene at a time. Using fixations and saccadic eye movements to sample the environment is an old strategy, in evolutionary terms, but this strategy requires an elaborate system of visual processing in order to create the rich perceptual experience. One of the most basic feats of the visual system is to correctly discern whether movement on the retina is owing to real motion in the world or rather to self-movement (displacement of our eyes, head or body in space). The retinal image is never particularly stable. This instability is owing to the frequent occurrence of tremors, drifts, microsaccades, blinks and small movements of the head. The perceptual cancellation of ocular drift appears to primarily occur through retinal mechanisms, rather than extra-retinal ones mechanisms. Attention also plays a role in visual stability, most probably by limiting the number of items that are fully processed and remembered.

Visual pursuit means the movement of the eyes in response to visual signals. Smooth pursuit eye movements allow the eyes to closely follow a moving object. It is one of two ways that humans and other visual animals can voluntarily shift gaze, the other being saccadic eye movements. Pursuit differs from the VOR, which only occurs during movements of the head and serves to stabilize gaze on a stationary object. Most people are unable to initiate pursuit without a moving visual signal. The pursuit of targets moving with velocities of greater than 30°/s tend to require catch-up saccades. Most humans and primates tend to be better at horizontal than vertical smooth pursuit, as defined by their ability to pursue smoothly without making catch-up saccades. Most humans are also better at downward than upward pursuit. Pursuit is modified by ongoing visual feedback.

Frequency, in this disclosure and claims, means the number of cycles (typically rotational cycles) per second. Frequency is expressed in Hertz, which is abbreviated as Hz. VOR, DVA, DVS, RIS, and other ocular reflexes are typically measured at frequencies that include at least one frequency in the range of 0.01 Hertz (one cycle every 100 seconds) to 15 Hertz (15 cycles per second), with many prior art systems at least measuring in the range of 0.1 Hertz (one cycle every 10 seconds) to 1.28 Hertz (slightly more than one cycle per second).

Gain, in this disclosure and claims, means the measured ratio of eye movement velocity to head movement velocity. More specifically, for example, the "gain" of the VOR is defined as the change in the eye angle divided by the change in the head angle during the head turn. The gain of the horizontal and VOR is usually close to 1.0, but the gain of the torsional VOR (rotation around the line of sight) is generally low. Eye and head movements during the VOR are oppositely directed, and if eye velocity exactly mirrors head velocity, the gain remains at 1 during the entire head movement. This, however, is only true, if one assumes zero latency between head and eye movements. In fact, the latency of the VOR is typically about 10-20 milliseconds. A gain of 1.0 and a phase shift of 180° indicate perfect VOR function, meaning that the eyes move synchronously with head movement but in the opposite direction. For a healthy person, the VOR is at its best during sinusoidal head oscillations or rotations in the range of 2 Hz to 6 Hz as encountered in natural locomotion. VOR is less efficient at the extremely low frequencies (less than 2 Hz) of head movement. The gain of the translational VOR has to be adjusted for distance, because of the geometry of motion parallax. When the head translates, the angular direction of near targets changes faster than the angular direction of far targets. If the gain of the VOR is abnormal (for example when the eye muscles are weak, or if a person has taken certain drugs or had a traumatic brain injury resulting in a balance disorder), then head movement results in image motion on the retina, resulting in blurred vision. Under such conditions, motor learning adjusts the gain of the VOR to produce more accurate eye motion. This is what is referred to as VOR adaptation.

Phase (or phase shift), in this disclosure and claims, is a measurement of the relationship between eye movement velocity and head movement velocity at a particular oscillation frequency of the head. More specifically, phase shift is an offset in the timing of eye movement relative to head motion at a specific rotational oscillation frequency. The phase shift of the VOR is a second useful measure of the vestibular system and represents the timing relationship for the eye and head position. Ideally, eye position should arrive at a point in time that is equal with the oppositely directed head position. By convention, this is described as a zero phase shift. Phase is a parameter that describes the timing relationship between head movement and reflexive eye response. When the head and eyes are moving at exactly the same velocity in opposite directions, they are said to be exactly out of phase, or 180°. If the reflex eye movement leads the head movement, a phase lead is present, and if the compensatory eye movement trails the head movement, a phase lag is present.

Symmetry (and asymmetry), in this disclosure and claims, is a comparison of eye response or (reflex) in opposite directions. The words symmetry and asymmetry can be used interchangeably. Symmetry is typically expressed as a percentage. For example, the horizontal symmetry (or asymmetry) can be expressed using the following equation:

$$Symmetry = 100 \times ((Left\ velocity) - (Right\ velocity)) / ((Left\ velocity) + (Right\ Velocity))$$

Horizontal symmetry is related to yaw of the eyes. The equation for vertical symmetry (or asymmetry) is the same as the above with the words "up" and down substituted for right and left. Vertical symmetry is related to pitch of the eyes. Symmetry can also be measured for head rotation as viewed from the front (i.e. roll) and the associated roll (or torsion) of the eyes on a clockwise versus a counter-clockwise direction when viewed from the front. Symmetry is typically evaluated at the same frequencies as gain and phase. It can be performed for one eye or both eyes. Symmetry can also be described as a comparison of the slow component of the nystagmus when rotated to the right compared with rotation to the left. Asymmetry can be present in some cases of unilateral vestibular hypo-function, as well as in other forms of vestibular dysfunction.

A Fourier transform is used to convert any arbitrary motion into a series of sinusoidal motions at various frequencies. By doing this, a graph of input motion and output motion as a function of time (i.e. in the time domain) can be converted into a graph that shows the gain and phase response plotted as a function of frequency (i.e. the response in the frequency domain). A Fourier transform can be used to convert a comparison of random natural motion (linear and/or rotational) of the head and the eyes into information that shows the gain and phase response of the eyes to movement of the head (i.e. VOR). Thus, Fourier transforms make it possible to measure VOR in a non-clinical environment without having to provide head excitations at specific frequencies.

Torsion refers to the process of being rotated about an axis. As it relates to the eye movement, it means any rotation of the vertical corneal meridians (any line bisecting the cornea through its apex). Torsional eye movements can be defined in two different ways, namely as a rotation about the line of sight and as a rotation about an antero-posterior (forward-to-backward) axis that is fixed in the head. The most natural definition of a torsional eye movement is as a rotation about the line of sight. The line of sight is the imaginary line that connects the eye with the fixation target. When the eye rotates about this line, the eyes remain fixated on this same target. When the eye makes any horizontal and/or vertical gaze shift, the line of sight and, therefore, the axis of rotation for torsion, shifts as well. For example, if one looks straight ahead, eye torsion occurs about an antero-posterior (forward-to-backward) axis. If one looks leftward, the axis of rotation for eye torsion is also rotated leftward.

If we look at a certain object, a projection of the object is made on the retina of the eyes. This projection is called the retinal image. If any torsion is made in an eye, for example in clockwise direction, then the retinal image of the object rotates by exactly the same amount, but in counterclockwise direction. Functions of eye movements in general include 1) the tracking of moving objects (pursuit), 2) the redirection of fixation to points of interest (saccades), 3) stabilization of the retinal images and 4) the maintenance of correspondence of the images in both eyes. Torsional eye movements are potentially important in the last two of these functions.

Six degrees of freedom (6 DoF) refers to the freedom of movement of a rigid body in three-dimensional space. Specifically, the body is free to move forward/backward, up/down, left/right (translation in three perpendicular axes) combined with rotation about three perpendicular axes, often termed pitch, yaw, and roll.

An example of six degree of freedom movement is described as Translation: Moving up and down (heaving); Moving left and right (swaying); Moving forward and backward (surging) and Rotation: Tilting forward and backward (pitching); Turning left and right (yawing); Tilting side to side (rolling). Translational motion is movement of an object without a change in its orientation relative to a fixed point, as opposed to rotational motion, in which the object is turning about an axis.

Pitch is referred to as rotation about the side-to-side axis (also called the lateral axis or transverse axis), which by example, passes through an airplane from wing tip to wing tip. Pitch changes the vertical direction the airplane's nose is pointing. A pitch motion is described as an up or down movement of the body, like that of bending forward or backward; or a nodding of one's head as if to say "yes."

The longitudinal axis, using the example of a plane, passes through the plane from nose to tail. Rotation about this front-to-back is called bank or roll. Another example of a roll is the head tilting to the side toward the shoulder. A rolling motion is an up and down tilting movement of the head and shoulders.

Yaw refers to the rotation around the vertical axis. A yaw motion of the head is described as a horizontal movement from side to side; or a shaking of one's head as if to say "no." When turning the head horizontally or vertically (i.e., yaw or pitch) the VOR maintains visual fixation on the object of interest throughout the head movement and thereby reduces the motion of the image on the retina. The semicircular canals in the inner ear detect rotary accelerations, such as when turning the head, while the otoliths detect linear accelerations during a translation, for instance, and through the earth's gravitation. The canals and the otoliths are the anatomic substrates for VOR eye movements.

2. PHYSIOLOGY

The VOR generates compensatory eye movements in response to head motion detected by the vestibular sense organs located in the inner ear. The oculomotor response to angular head movement is called the angular VOR (AVOR or VOR) and has been demonstrated for rotation in yaw, pitch, and roll. An oculomotor response to linear acceleration has been described for acceleration along the interaural axis, spinal axis, and nasal-occipital axis and has been called the linear VOR (LVOR). The VOR is crucial to the maintenance of gaze stability and visual acuity. Patients who have lost their vestibular systems suffer from illusory motion of the seen world (oscillopsia) during head motion and may have difficulty recognizing familiar faces while walking. Dysfunction within the VOR pathways may result in nystagmus, ocular misalignment, ocular torsion, and pathologic head tilt. All of these findings can adversely affect human performance to focus on a target of interest with rotational or translational movement or motion.

The visual, vestibular and proprioceptive systems are key sensory organ systems for maintaining balance. The corrective eye movement response is used to provide stable vision during the head movements of walking, running, driving and all of the other normal movement activities. The visual system receives sensory input from the eyes to determine body position in space and with movement. The vestibular system receives sensory input from the inner ears. The inner ear is sensitive to gravity and detects both linear and angular movements. The proprioceptive system provides information about the relative position of body segments to one another and about the position of the body in space. When these three systems are functioning properly, balance problems do not normally exist. In addition, these three systems are mutually interdependent and provide redundancy, which permits balance to be maintained if one of these three primary systems fails. Three resultant mechanisms created by the visual, proprioceptive, and vestibular systems include the oculomotor system, VOR, and the vestibular spinal reflex. The simple eye movement response (e.g. VOR) is an indicator of the function of one part of the balance system.

The oculomotor system keeps images centered on the fovea, which is the area of high visual acuity. DVA is the ability of an individual to quickly fixate and re-fixate on different and moving targets. The three components of this oculomotor system controlled by the central nervous system include: saccades, smooth pursuit, and optokinetics. The saccadic system is responsible for rapidly directing the fovea to a target of interest in visual space. This system creates a conjugate movement of the eyes, a saccade that brings the fovea on target within a fraction of a second. Saccades are tested by having an individual keep his or her head still while moving only his or her eyes from target to target (typically, the target will appear middle, then left, middle, then right, etc.). The smooth pursuit system is concerned with keeping the fovea on a moving target once that target has been located. Smooth pursuit is tested by having a person keep his or her head still while smoothly following a moving target with his or her eyes. The optokinetic system detects motion using peripheral vision. The optokinetic system is tested by having a person keep his or her head still while trying to focus on targets that move rapidly across the patient's field of vision, disappearing on one side and reappearing on the other.

As noted previously, the VOR is a reflex eye movement designed to stabilize images on the retina during head movement by producing eye movement in the direction equal and opposite to head movement. If the position of the head is altered, this reflex system keeps the eye looking in the same direction as it did before the movement. The head movement of interest typically ranges from 0.1 Hz (nearly still) up to 15 Hz. The VOR elicits eye movements in response to head movements in all directions, including horizontal, vertical, and rotational head movements. When head motions are above 2 Hz (two back and forth motions in one second), the VOR is essential to helping maintain balance, because when head motions reach that speed, the smooth pursuit system, the saccadic system, and the optokinetic system cannot effectively function at that speed, and the VOR takes over. The VOR has often been measured in the dark by some to distinguish eye movements driven by vestibular stimuli from eye movements driven by visual stimuli. The performance of the VOR can be measured by the gain, which is defined as the amplitude ratio between eye and head velocities. If a person's VOR gain is poorly calibrated, then head movements result in image motion on the retina, causing blurred vision. Under such conditions, motor learning adjusts the gain of the VOR to produce more accurate eye motion. Such adjustments are needed throughout life, as neurons and muscles develop, weaken, and die or when a new pair of eyeglasses changes the magnification of the visual field. Depending on the relative direction of head motion and image motion, the gain of the VOR can be adaptively increased or decreased. An increase in VOR gain is induced by image motion in the direction opposite that of the head (gain up stimulus) and a decrease in VOR gain is induced by image motion in the same direction as the head (gain down stimulus).

The VOR needs to be fast: for clear vision, head movement must be compensated almost immediately; otherwise, vision corresponds to a photograph taken with a shaky hand. To achieve clear vision, signals from the semicircular canals are sent as directly as possible to the eye muscles. The connection between the semicircular canals and the eye muscles is made using only three neurons, and is called the three-neuron arc. Using these direct connections, eye movements lag the head movements by less than 10 ms, and thus the VOR. The VOR acts at short latency to generate eye movements that compensate for head rotations to preserve clear vision during locomotion. The VOR is the most accessible gauge of vestibular function. Evaluating the VOR requires application of a vestibular stimulus and measurement of the resulting eye movements.

More specifically, the VOR serves to compensate eye movements effectively for head movements at frequencies in the range of 0.1-15 Hz, especially if the head movement is voluntary—However, the VOR is less accurate at lower frequencies, especially those lower than 0.1 Hz, where the gain drops significantly and a phase lead appears. The optokinetic reflex has the opposite performance characteristics. It has longer latency (due to the fact that it uses visual input and not inner ear stimulation) than the VOR, but at low frequencies (i.e. less than 0.1 Hz), it has near unity gain and no phase difference. From 0.1 Hz to approximately 1 Hz, the optokinetic reflex begins to lose gain and develop a phase lag due to higher latencies. At higher frequencies it cannot effectively compensate due to its relatively long latency and low gain compared to the VOR. Therefore, the combination of the two mechanisms allow for maximal image stabilization all the way from the lowest frequencies (governed mostly by the optokinetic reflex) to the highest frequencies (governed mostly by the VOR). There is another aspect of the VOR/optokinetic reflex combination that contributes to improved performance over either system alone. This aspect is a timing issue: time of onset and time of offset. As previously mentioned the VOR has a very short latency (onset time) while the optokinetic reflex has a longer latency. The VOR then allows for a faster reaction time even at lower frequencies. But the VOR will eventually decay during constant, zero-acceleration rotation due to the elasticity of the cupula within the semicircular canal. Although effectively extended through central processes, the time constant of pure VOR related nystagmus in humans is approximately 25 seconds. The optokinetic reflex, however, has a long latency but no time constant, as its response does not decay with repeated stimulation of the retina by an optical flow. Therefore, as the VOR decays, the optokinetic reflex is building up, creating a continual, seamless stabilization of most images on the retina.

The vestibular spinal reflex adjusts posture for rapid changes in position. It helps the maintenance of balance with rapid head movement. At least two of the three balance-related sensory organ systems (vestibular, visual, and proprioceptive) are necessary to maintain balance, albeit with some difficulty if one of the three is dysfunctional. However, even though the interdependence of the systems may lead to balance compensation when there is a loss of at least one system, other brain functions may suffer as a result. In particular, cognitive difficulties can be caused by disturbances in the balance mechanisms. These difficulties are felt to be a result of suppression of the reticular activating system in the brainstem. Since the areas of the brain that usually carry out thought and memory functions now must focus on balance, the brain sacrifices some of its cognitive function. This leads to a change in mental abilities of the individual. When an individual appears to be suffering from a balance disorder, the individual can be tested to determine which of the three systems exhibits abnormalities. Numerous tests have been developed to assess the function of these three systems.

To understand more in detail, the VOR starts in the vestibular system, where semicircular canals get activated by head rotation. During rotational movements of the head, the endolymphatic fluid within the semicircular canals shifts because of its inertia. This deflects the cupula. Endolymphatic flow toward the ampulla is excitatory in the horizontal canals, while flow away from the ampulla is excitatory in the superior and posterior canals. A signal of rotation or translation impulses are sent to the vestibular nerve (cranial nerve VIII) through Scarpa's ganglion and end in the vestibular nuclei in the brainstem. The afferent nerves from the ampulla actually carry both excitatory and inhibitory signals to the 4 major vestibular nuclei: medial vestibular nucleus, lateral vestibular nucleus, inferior or descending vestibular nucleus, and superior vestibular nucleus. Different regions within each of the nuclei project to the oculomotor nuclei (cranial nerves III, IV, and VI), which control the muscle movements of the eyes.

Efferent signals from these nuclei then result in contraction and relaxation of the appropriate ocular muscles. Excitation of the superior canal results in contraction of the ipsilateral superior rectus and contralateral inferior oblique muscles and relaxation of the ipsilateral inferior rectus and contralateral superior oblique muscles, which results in an upward torsional eye movement. Excitation of the posterior canal results in contraction of the ipsilateral superior oblique and contralateral inferior rectus muscles and relaxation of the ipsilateral inferior oblique and contralateral superior rectus muscles. This results in a downward torsional eye movement. Finally, excitation of the lateral canal results in contraction of the ipsilateral medial rectus and contralateral lateral rectus muscles and relaxation of the contralateral medial rectus and ipsilateral lateral rectus muscles. This results in a horizontal eye movement toward the opposite ear.

In addition to these direct pathways, which drive the velocity of eye rotation, there is an indirect pathway that builds up the position signal needed to prevent the eye from rolling back to center when the head stops moving. This pathway is particularly important when the head is moving slowly, because in this situation position signals dominate over velocity signals. The eye muscles require this dual velocity-position drive. The integrator for horizontal eye position is in the nucleus prepositus hypoglossi in the medulla, and the neural integrator for vertical and torsional eye positions is in the interstitial nucleus of Cajal in the midbrain. The same neural integrators also generate eye position for other conjugate eye movements such as saccades and smooth pursuit. The vestibulo-cerebellum compares input from visual and vestibular sensors and mediates changes in the VOR after vestibular injury or change in visual function.

In addition to oculomotor projections, the vestibular nuclei send fibers to the vestibulo-cerebellum, the nucleus prepositus hypoglossi, and the cells within the paramedian tracts. The nucleus prepositus hypoglossi is crucial for the maintenance of a steady gaze, while the cells within the paramedian tracts are responsible for relaying information to the vestibulo-cerebellum, specifically the flocculus. Reciprocal projections to and from the cerebellum assist in fine motor control of eye movements. The latency of action of the rotational VOR is 7-15 milliseconds, which is the time required for the eyes to respond in an equal, but opposite, manner to the motion of the head. This time is remarkably fast compared with the latency for visually mediated eye movements, which is longer than 75 milliseconds. Cerebral function may also be responsible for the modification of the VOR and the ability to suppress the VOR. Specifically, injuries to the parietal vestibular cortex and the ocular gyms appear to interfere with visual suppression of the VOR. In particular, the right temporoparietal cortex is believed to be involved in the modulation of the VOR. This region has been shown to be sensitive to the effects of sleep deprivation, particularly with respect to VOR gain during step testing.

The translational VOR pathways are activated in response to stimulation of the otolithic organs. The utricle responds to lateral translation stimuli, whereas the saccule responds to vertical translations. Translational VOR pathways also appear to be mediated by projections to the ocular motor nuclei via projections from the vestibular nuclei. Specifically, excitation of the utricular macula results in contraction of the ipsilateral superior oblique, superior rectus, and medial rectus muscles and relaxation of the contralateral inferior oblique, inferior rectus, and lateral rectus muscles.

Having described the normal VOR system, it is important to discuss VOR dysfunction. Similar to all other systems in the body, most individuals are not aware of the presence of the VOR until it malfunctions. Acute VOR dysfunction may manifest in several different ways, depending on the anatomical location of the lesion or lesions, and may result from labyrinthine disorders or disorders of the central vestibular system. Studies have shown that people with a unilateral peripheral vestibular lesion may exhibit asymmetric responses to rotation. On the other hand, people with a compensated unilateral lesion show a characteristic pattern of decreased gain and increased phase lead at low-frequency stimulation. Bilateral peripheral vestibular lesions are characterized by low gain and phase lag as determined by sinusoidal testing. These patients commonly report oscillopsia, a sensation of vertical or horizontal motion of the environment, or persistent unsteadiness, especially in the dark. Rotational chair testing is ideal in the assessment of these patients because, unlike caloric testing, higher frequencies are tested and both labyrinths are simultaneously stimulated. This allows for an accurate determination of remaining vestibular function, which is important for determining a course of treatment.

Central vestibular deficits may also affect the VOR. Gains may be increased in some individuals with cerebellar deficits. Cerebellar atrophy, on the other hand, may result in a disorganized nystagmus pattern with beat-to-beat variabilities in amplitude. Lesions within the parietal vestibular cortex and the ocular gyms may interfere with the ability to suppress VOR visually. High-velocity angular VOR function can also be affected by post-blast exposure, as studied in military service members.

Although an impaired VOR is generally the result of an injury to the vestibular system, the VOR may also be affected by systemic disease processes such as migraines, depression, and anxiety disorders. With migraine vestibulopathy, one may see an elevated gain with visually enhanced VOR, a testing paradigm where the VOR rotation stimulus is done in a lighted (i.e., visually enhanced) environment rather than in the traditional dark booth. Patients who experience anxiety disorders may have an increased vestibular sensitivity resulting in significantly higher VOR gains and shorter time constants. Finally, those patients with major depression have been shown to have hypoactive vestibular nuclei, resulting in a decrease in the slow phase of the nystagmus.

Other common issues can also adversely affect the VOR and DVA. Ethanol consumption can disrupt the VOR, reducing DVA and retinal visual stability. Like the VOR, the DVA may be affected by systemic disease processes such as migraines, depression, and anxiety disorders. Alertness, poor sleep or inadequate sleep and performing in low light levels can adversely affect the VOR/DVA. In a provocative motion environment, such as flight, vibration, angular motion and translation are common causes of destabilization of the retinal image, and can, in certain circumstances, be of sufficient severity to prevent the pilot from reading the instrument. The ability of a pilot to perceive important visual cues, either from the external world or from flight deck instruments, can be degraded by factors that impair either the quality of the retinal image or the transduction process of the image by the sensory cells of the retina.

There are technical reasons, such as goggle slippage with testing, which causes eye-to-head movement velocity asynchrony in both head movement directions rather than systematic eye velocity saturation in just one direction, and can adversely affect the measurement of VOR and/or DVA.

When the VOR or DVA are abnormal, which occurs during the early stage after unilateral vestibular loss, recovery is delayed if the visuomotor experience is prevented. Avoidance of movements and body positions that provoke vertigo also retards recovery. Factors affecting recovery of the VOR and/or DVA when it is reduced include medications, visual and somatosensory inputs, stage at which treatment is commenced, daily exercise duration, symptom intensity, the site of the lesion, the patient's age, and psychogenic factors. The use of centrally acting medications such as vestibular suppressants, antidepressants, tranquilizers, and anticonvulsants also prolong the mean duration of therapy required to achieve the eventual outcome.

There can be factors that enhance the VOR and RIS or DVA. Increased mental activity, ortho-optho (eye movement) exercises, head/eye exercises, lack of drugs/alcohol, rest and better lighting in the area of performance all will enhance the VOR and/or DVA. With any of these factors better RIS and retinal visual stability can be achieved.

3. CLINICAL TESTING

Historically, VOR, DVA, and DVS measurement have been performed in a controlled environment, typically a clinical setting. VOR, DVA, and/or DVS measurement has typically not been applied to non-clinical testing of natural motion in an ambulatory environment, such as "on the field" measurement of athletic performance, or day-to-day military, law enforcement, driving, competitive shooting, or industrial environments. Non-clinical testing in an ambulatory occupational environment can provide a more relevant and objective determination of a person's actual performance. Non-clinical testing can also measure the person's typical ambulatory occupational environment. In athletics, for example, on-site testing can help coaches select players on a particular day. In a military applications field testing can help select pilots or special ops personnel immediately before a mission. Currently some occupations (such a flying and competitive sports) do drug testing to evaluate performance, but athletic sports in professional, college, high school and even at lower levels don't currently evaluate the head movement with eye fixation ability of the players. Similarly, persons who are in an environment with high levels of head/eye movement activity are currently not evaluated before performing specific activities.

Techniques used to measure VOR in clinical settings include (1) stimulating the inner ear with caloric irrigation using air or water and (2) rotational testing. There are four main types of rotational testing: (2a) rotational testing by fixing the head to a rotationally moving chair, (2b) actively moving the head only, using an external signal such as a metronome with video recording (2c) passively moving the head only, with the assistance of another person using video recording and (2d) active head shake testing, using Frenzel glasses, with an observer looking at eye movements.

Caloric irrigation produces a convection current of endolymph when the canal is oriented vertically because endolymph sinks when cooled and rises when warmed. Thus, cool irrigation causes nystagmus (which is seen with video recording as rapid eye twitching) away from the ear and warm irrigation causes nystagmus toward the ear. Caloric irrigation is inherently limited by the effectiveness of heat transfer between the external and inner ear. A small or occluded external ear canal reduces the intensity of the caloric stimulus to the inner ear. Consequently, a reduced response may result from technical issues such as inadequate irrigation rather than vestibular hypo-function.

Rotational testing can be performed using active (volitional) or passive rotations with video recording. Rotational testing can be low frequency or high frequency. Rotational testing can use head only or whole body rotations (which occurs in a rotary chair). There are two main advantages of rotational testing over caloric testing. First, rotational testing does not depend on the effectiveness of thermal energy transfer across the middle ear and through the temporal bone. Second, rotational testing allows precise application of multiple frequencies of rotational stimuli, whereas caloric testing is equivalent to a single, very low frequency (0.003 Hz) vestibular stimulus. There are two main disadvantages of rotational testing. One disadvantage is that rotation affects both ears simultaneously, making it less helpful in detecting unilateral lesions. Another disadvantage is the cost of the equipment.

The stimuli during rotational testing are usually either impulses or sinusoidal rotations. Impulse rotations demand a rapid acceleration (usually about 100°/second/second) to a constant speed and, after the nystagmus fades away, a sudden stop during which the nystagmus is again recorded. Sinusoidal rotations are performed by rotating the patient's head or body from side to side, so that head movement recordings appear as a series of sine waves. The frequency of these sinusoidal rotations is measured in cycles/second, also known as Hertz (Hz). VOR rotary testing is done in darkness or with the eyes closed to avoid the influences of vision on the VOR. The VOR can also be suppressed by fatigue or inattentiveness. Consequently, mental alerting tasks (e.g., mental arithmetic) are used to maximize VOR responses. The purpose of rotational testing is to determine whether dizziness may be due to a disorder of inner ear or brain. There are three parts to the test. The chair test measures symptoms of dizziness (jumping or back and forth movement of the eyes, called nystagmus) while being turned slowly in a motorized chair with the head fixed. Persons with inner ear disease become less dizzy than do normal persons. The fixation test measures nystagmus while the person is being rotated, while they are looking at a dot of light that is rotating with them.

Rotary chair testing provides a known stimulus input and measuring the response output. The ratio of the output to input is called the "transfer function". There are many reasonable protocols for the input. For a linear system, any protocol that includes a reasonable selection of frequency components should result in the same result, which is a gain and time constant. As there are nonlinear processes in the vestibular system (such as prediction), the various methods may not always produce the same results. At present, most laboratories use either sinusoidal testing or step testing.

The sinusoidal test protocol involves rotating the chair so that it moves sinusoidally. Because the derivative of a sine is another sinusoid, chair position, velocity and acceleration all change sinusoidally. Ordinarily one chooses a desired peak chair velocity, such as 60 deg/sec, and one also picks a series of frequencies to test covering about 0.1 to 1 Hz. These frequencies cover the range of responses where gain and phase show their greatest variability when there is disease. A variant of sinusoidal testing is "sum of sines" (SOS) where one mixes together a group of sine waves to make the input less predictable. Although the SOS appears complex, it can be analyzed using standard mathematical methods (i.e. Fourier analysis). A "Bode plot" is essentially a semi-logarithmic plot of vestibular gain and phase and is generally used to present results. A powerful motor is needed to attain the higher frequencies, and for this reason, sometimes testing will only include lower frequencies or the peak velocity will be reduced at the highest frequency.

The step test involves suddenly changing chair velocity (with an impulse of velocity). Step responses provide roughly equivalent gain/phase information, as does sinusoidal testing. Step responses have many problems. They require a powerful chair to provide a high acceleration transient. They may be less reliable as well as somewhat more stressful to the patient, and for this reason, sinusoidal testing is generally preferred. Motion sickness is sometimes associated with prolonged vestibular responses, and for this purpose, step responses may be preferable to sinusoids. Practically though, nausea is unusual in sinusoidal testing and this is not a strong consideration.

There are several other alternative procedures involving rotation of the head to evaluate the VOR. Active head movement allows the user to self-move the head back and forth with an external stimulus such as the sound of a metronome (autorotation). With each click of the metronome the person moves the head. The frequency of the clicking and therefore the head movements will gradually increase. Passive head movement, with an assistant moving the head, may provide more valid responses by turning the head at unpredicted moments. Both of these tests provide high-frequency information compared to being seated in a rotary chair (which provides low frequency data) and measure something a little different, which is the contribution of the inner ear, cognitive input, and neck inputs to nystagmus rather than the contribution of the inner ear alone. The Vestibular Autorotation Test is a computerized test that measures the horizontal (sideways rotation or yaw) and vertical (up/down rotation of the face, also known as pitch) VOR with the use of active head movements in the range of 0.1 Hz to 15 Hz to obtain gain and phase.

The VOR, when tested by passive rapid movement of the head using an assistant, is referred to as the Rapid head impulse test or Halmagyi-Curthoys-test. As the rapid head impulse test is performed, the head is rapidly moved to the side with force, and the VOR will be controlled if the eyes succeed to remain looking in the same direction. When the function of the balance system is reduced, for example in the right ear by a disease or by an accident, quick head movement to the right cannot be sensed properly. As a consequence, no compensatory eye movement is generated, and the person cannot fixate a point in space during this rapid head movement.

Active Head Shake Test: Rapid horizontal head shaking by oneself for 15 to 20 seconds occasionally results in horizontal post-headshake nystagmus usually (but not always) directed away from the side of a unilateral vestibular loss. When done in the office setting Frenzel's glasses are typically worn while doing this test to prevent ocular fixation that can suppress the nystagmus. Headshake nystagmus is generally thought to occur when asymmetries in resting vestibular tone are exaggerated via brainstem control mechanisms.

4. LIMITATIONS OF THE PRIOR ART FOR A NON-CLINICAL ENVIRONMENT

To measure the VOR under natural conditions, both head and eye movements must be measured accurately during active natural head motion in an ambulatory setting. Prior art systems for tracking head and eye movements have serious limitations for use during free head movements in a non-clinical and non-laboratory setting. Prior art systems for tracking eye movement include electro-oculography, magnetic scleral search coils, infrared video-nystagmography, and other video eye-tracking devices. Prior art head motion can come from a rotary chair that is excited at a specific set of frequencies and amplitudes. It is also known to measure head motion using a magnetic position transducer. These prior art techniques do not allow for a full self-contained portable system for measuring or enhancing the VOR or other eye responses in real life environments.

Electro-oculography (EOG) is the most commonly employed method of recording eye movements. This technique measures the change in corneo-retinal potential using electrodes placed around the inner and outer canthi of the eyes. It is limited by poor sensitivity, poor vertical and binocular measurements, artifacts introduced by muscle action potential, and electrical noise introduced by electrode movement and other physiological and environmental sources. To test the VOR reliably, it is important to determine that other types of eye movements are normal for two reasons. First, proper interpretation of the VOR responses depends on intact eye movements. Second, abnormalities of eye movements can themselves be useful in localizing neurologic abnormalities. EOG permits recordings of the direction, amplitude, and velocity of eye movements. Torsional eye movements are not recorded with EOG.

Magnetic search coil are a reliable eye movement recording technique, but it requires the patient to wear a specialized contact lens during testing and is available for clinical use only in a few institutions. Magnetic scleral search coils are circles of electrically conductive wire that are embedded into tightly fitting contact lenses or a rubber ring that adheres to the white portion (sclera) of the eye. They can also be surgically implanted in the sclera (white portion) of the eye. Alternating magnetic fields are then generated by electromagnets (field coils) positioned around the eye. Through magnetic induction, electric currents are generated in the search coils. The polarity and amplitude of the current generated varies with the direction and angular displacement of the eye. By measuring these values, the position of the eye can be determined. Magnetic scleral search coils can be applied to one or both eyes. In order to detect eye orientation in more than one dimension (e.g. up/down versus left/right), multiple electromagnets must be oriented orthogonally to one another. Each electromagnet must generate a field using a different frequency in order to allow a computer to determine the displacement in multiple dimensions. A second search coil could be added to measure torsional rotation of the eye. Magnetic scleral search coils cannot be used to measure free head motion due to the requirement that the search coils (and therefore the eyes) must remain close to the center of the magnetic field generated by the field coils. Use of this technique is also limited by the inability to make measurements of linear motion of the head. Furthermore, search coils have an invasive nature.

Infrared video nystagmography is an alternative method of determining eye movements that utilizes infrared cameras positioned to detect movement of the eyes in darkness. Horizontal eye movements are the most important and easiest to record because vertical eye movements are prone to blinking and eyelid movement artifacts. However, vertical eye movements should be recorded to help determine vertical nystagmus and blinking that may affect horizontal channel recordings. Torsional eye movements can be seen on infrared video recordings.

Other video eye-tracking devices can provide good comparable results to the scleral search coil method for measuring eye movements. The main disadvantage of video recordings compared with coils has been their limited sampling frequency. This is especially of importance when investigating fast eye movements such as saccades or responses to impulsive vestibular stimulation where accurate latency and gain measurements over a short time span are required. Another disadvantage of infra-red (IR) video systems is the difficulty in tracking eye positions in the dark because of large pupils and increased occlusion of the pupils by eyelids. If eyelashes or droopy eyelids partly occlude the pupil, proper detection of eye position may be deteriorated. Also, dark eyelashes may be problematic, because these may be confused with the pupil. With IR video systems, subjects generally cannot wear glasses due to obstruction by the head device. On the other hand, soft contact lenses do not seem to influence performance. In contrast, with scleral search coils only hard lenses can be used.

Studies of eye movements are often performed with the subject's head secured to the headrest of a chair in which is rotated (e.g. rotary chair testing). For example, the "gold standard" for testing the VOR has utilized low-frequency rotation (e.g., 0.1 Hz) of a subject in a horizontal plane. During natural movements such as locomotion, however, the head is subjected to rapid, unpredictable transient head perturbations with frequency components of up to 15 Hz. The long latency and poor high-frequency response of visual or cervical reflexes make them poorly suited for responding to these perturbations. A primary physiological role of VOR is to compensate for the high-frequency perturbations encountered during locomotion.

It is known to use a head tracker that uses a magnetic position transducer (see Allison et al, IEEE Transactions on Biomedical Engineering, November 1996). However, the transducer described by Allison requires the use of an external pulsed magnetic transmitter at a fixed location and therefore the system is not a self-contained portable system that can be used in any environment.

To summarize, current clinical vestibular eye response measuring equipment is highly specialized, bulky and requires a dedicated laboratory. There is need to have a portable system and method of measuring the VOR in real life environments, as this can predict quality of performance doing occupational activities.

BRIEF DESCRIPTION OF THE DRAWINGS

For a more complete understanding of the present invention and the advantages thereof, reference is now made to the following description taken in conjunction with the accompanying drawings in which like reference numerals indicate like features and wherein.

It should be understood that the drawings are not necessarily to scale. In certain instances, details that are not necessary for an understanding of the invention or that render other details difficult to perceive may have been omitted. It should be understood that the invention is not necessarily limited to the particular embodiments illustrated herein.

DETAILED DESCRIPTION

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment.

It should be understood that various changes could be made in the function and arrangement of elements without departing from the spirit and scope as set forth in the appended claims. Preferred embodiments of the present invention are illustrated in the Figures, like numerals being used to refer to like and corresponding parts of the various drawings. Specific details are given in the following description to provide a thorough understanding of the embodiments. However, it will be understood by one of ordinary skill in the art that the embodiments may be practiced without these specific details.

1. Overview of System and Method

Figure 1:
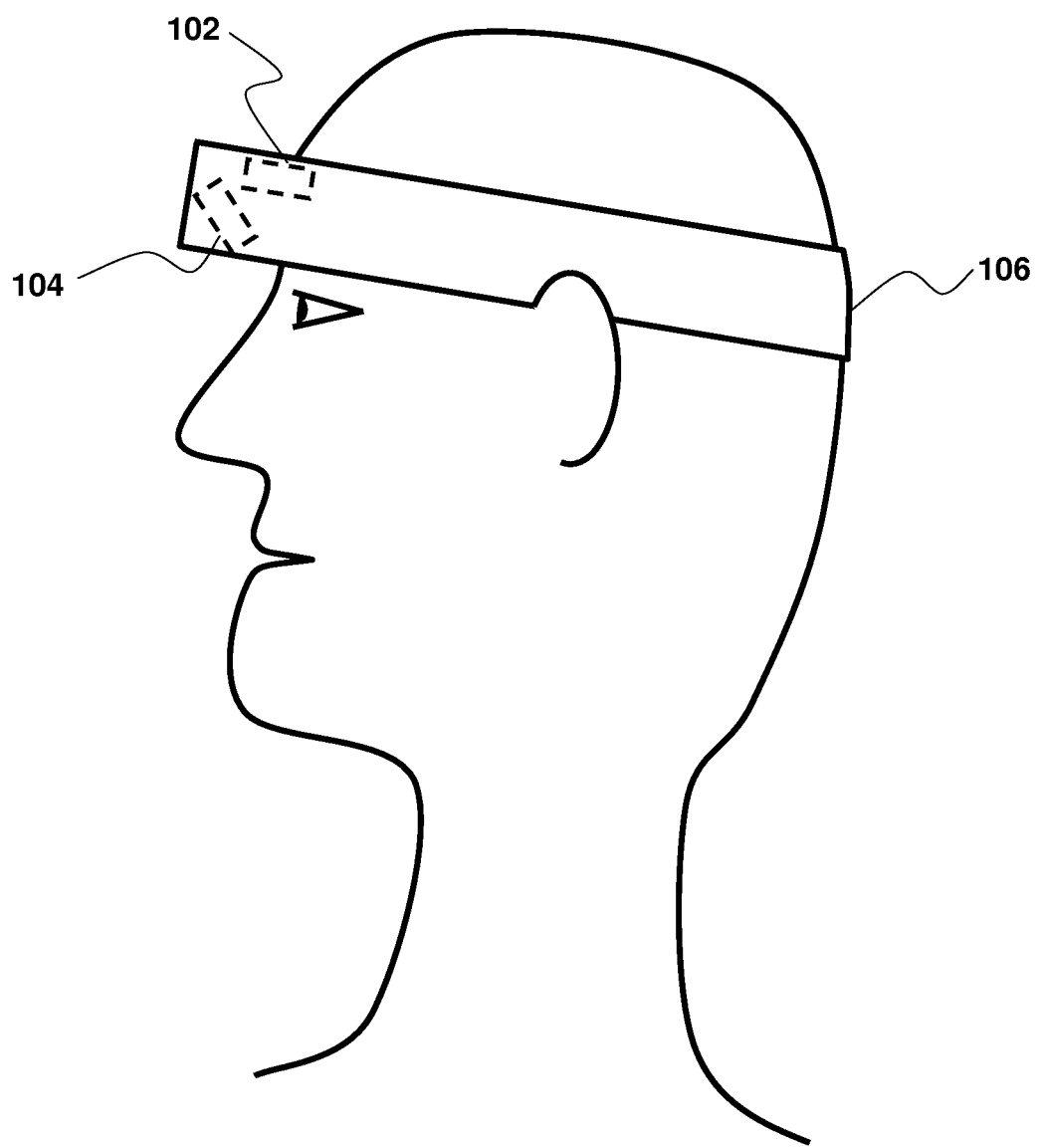
FIG. 1 illustrates a head-worn unit that can be used for measurement of physiologic conditions from the group of VOR, DVA, and/or DVS outside of a medical facility.

Referring now to the figures, FIG. 1 illustrates a portable self-contained head-worn unit that can be used for measurement of VOR, DVA, and/or DVS in an ambulatory occupational environment outside of a medical facility. The head-worn unit comprises a head attachment element shown at 106, a head orientation sensing element shown at 102, and an eye orientation sensor shown at 104. The head attachment element 106 is designed to fit snugly on the head so that all changes in head orientation result in an equal changes in orientation of the head-worn unit. The head orientation sensing element 102 is rigidly attached to the head-worn unit. In at least one embodiment, the head orientation sensing element 102 senses (is responsive to) pitch, roll, and/or yaw. Pitch can be described as upward or downward movement of the face. Roll can be described as rotation of the face when viewed from the front. Yaw can be described as leftward and rightward movement of the face when viewed from the front. The orientation sensor can be constructed from one or more elements or it can be monolithic. The orientation sensor can use one or more accelerometers, gyroscopes, magnetometers, or any other relative or absolute position, velocity, or acceleration sensing device capable of being understood by anyone skilled in the art. In one embodiment, the orientation sensor comprises a micro-electro-mechanical system integrated circuit. The head worn unit can also have a battery to power the entire system, which can be wirelessly charged.

Further referring to FIG. 1, in one embodiment, the eye sensor 104 is a video camera that is pointed at the person's eyes. The eye sensor can be responsive to vertical movement of the eyes (which represents pitch), rotation of the eyes (which represents roll), and horizontal movement of eyes (which represents yaw). There can be only one camera, that monitors only one eye, one camera with a wide angle, that can monitor both eyes, or two separate cameras, one to monitor each eye. There can also be multiple cameras, to monitor different areas of each eye (e.g. eye response sensors tracking pupil features and corneal reflection surface(s). The video camera can be positioned anywhere around the eye, and can utilize visible or invisible light.

Figure 2:
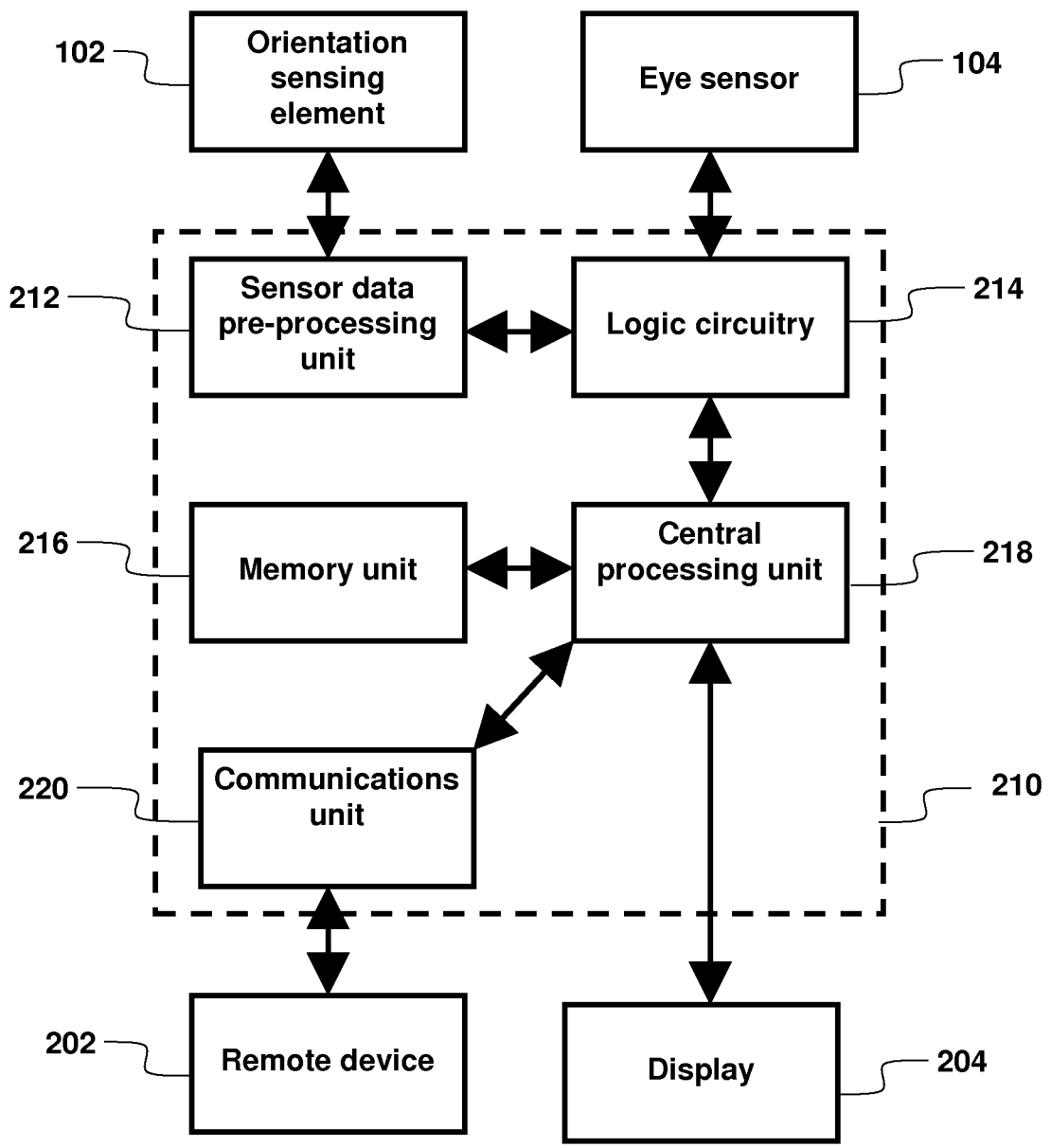
FIG. 2 illustrates an electronic circuit suitable for use as part of the system and method described in this disclosure.

In addition to the elements shown in FIG. 1, the head-worn unit can also include electronic circuitry that performs logical functions in comparing the signals from the head orientation-sensing element 102 and the eye sensor 104. The electronic circuitry 210 can further comprise a sensor data pre-processing unit 212, logic circuitry 214, a communications unit 220, a central processing unit 218, and a memory unit 216 as shown in FIG. 2. The electronic circuitry 210 can connect to a remote device 202 and a display 204. The memory unit 216 can store multiple readings and results, which can be used for data logging, tracking of multiple users, and tracking of performance at various times.

Figure 3A:
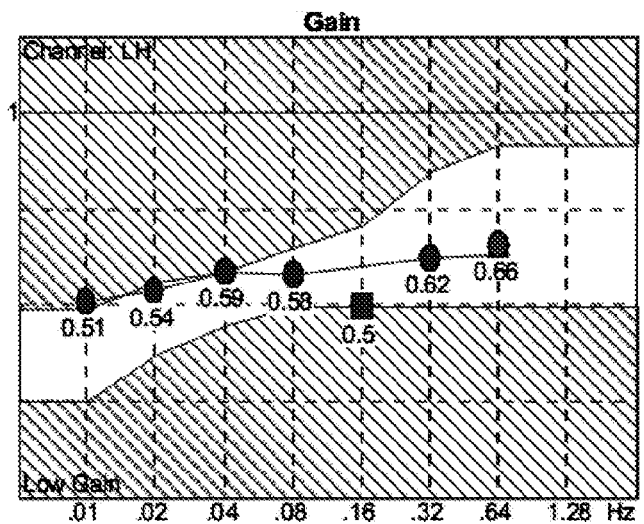
FIG. 3A illustrates an example of the left eye gain of a healthy person's vestibulo-ocular response to motion between 0.1 Hertz and 1.28 Hertz.
Figure 3B:
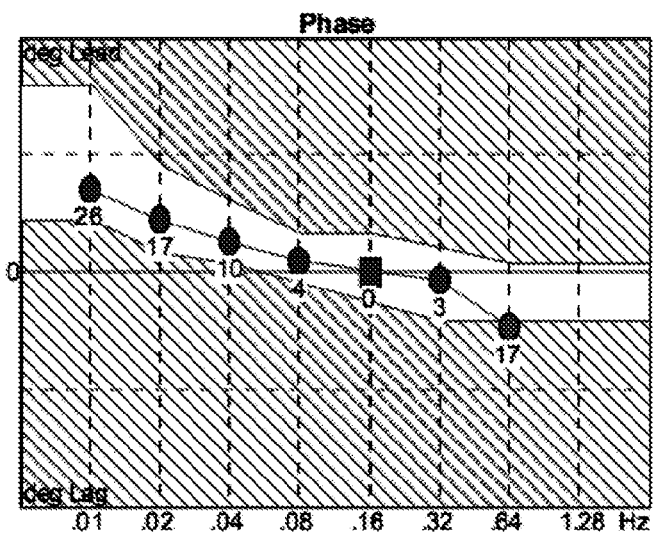
FIG. 3B illustrates an example of the phase lead and lag for a health healthy person's vestibulo-ocular response to motion between 0.1 Hertz and 1.28 Hertz.
Figure 3C:
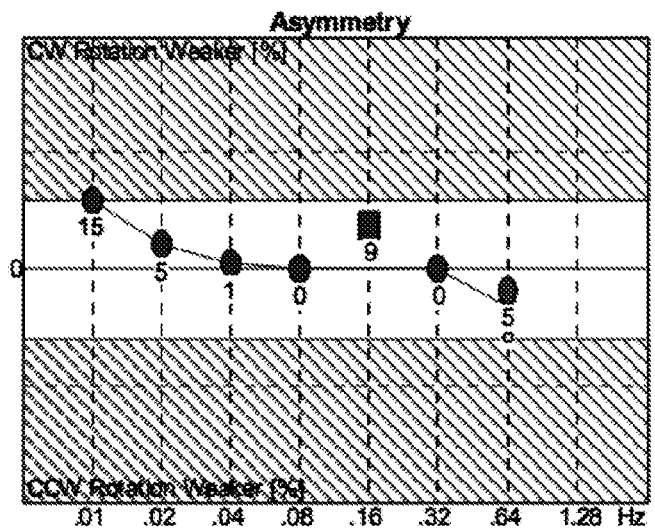
FIG. 3C illustrates an example of the asymmetry readings between counterclockwise and clockwise horizontal rotation of a healthy person's vestibulo-ocular response to motion between 0.1 Hertz and 1.28 Hertz.

FIG. 3A, FIG. 3B, and FIG. 3C. illustrate some typical eye responses to oscillation of a healthy person's head (e.g. vestibulo-ocular responses) in a horizontal plane at frequencies ranging from 0.1 Hertz (1 cycle every 10 seconds) to 1.28 Hertz (approximately 5 cycles every 4 seconds). More specifically, FIG. 3A. shows the gain at these frequencies, FIG. 3B shows the phase lead and lag at these frequencies, and FIG. 3C shows the relative symmetry (or asymmetry) between clockwise and counterclockwise oscillations. It should be noted that 0.1 Hertz to 1.28 Hertz is typical for the range of frequencies being used by prior art VOR testing systems. The embodiments described in this disclosure can include any frequency in the range of 0.01 Hertz (1 cycle every 100 seconds) to 15 Hertz (approximately 15 cycles every second).

Figure 4:
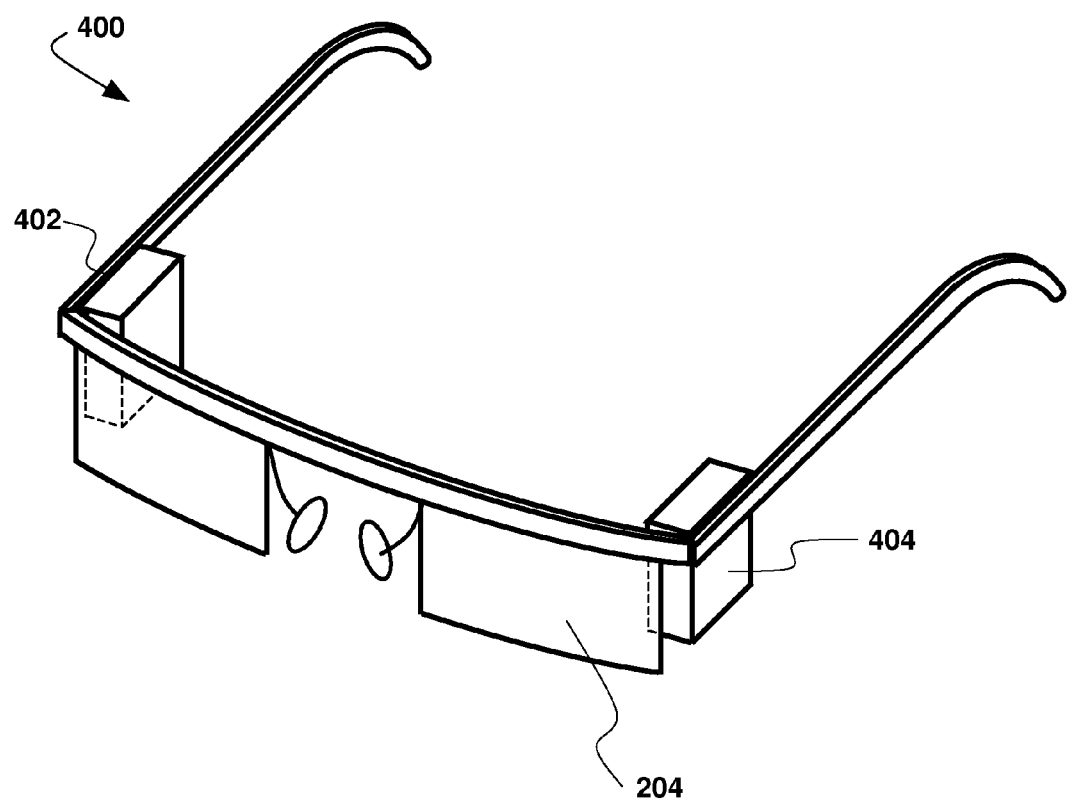
FIG. 4 illustrates an alternate embodiment of the head-worn unit in the form of a pair of glasses.

FIG. 4 shows an alternate embodiment of the head-worn unit 400 in the form of a pair of glasses that further comprise a display 204, a right side sensor unit 402, and a left side sensor unit 404. Each of the sensor units can comprise an eye sensor, an orientation sensor, and electronic circuitry as described previously.

2. Eye Tracking

To measure specific eye responses, such as the VOR, DVA and/or DVS both eye tracking and head tracking measurements are required. Embodiments of the present invention comprise an eye tracking system and method and a head tracking system and method. Eye tracking is the process of measuring either the point of gaze (where one is looking) or the motion of an eye relative to the head position. An eye tracker is a device for measuring eye positions and eye movement. Since the eyes are not located at the center of head rotation, any rotation of the head requires translation of the eye relative to visual targets. For targets at optical infinity, this translation does not require any compensatory movement. For near targets this translation becomes significant and compensatory eye movements are required for stable gaze and at close target distances. One must also compensate when measuring VOR and the compensation requires knowing the distance between the center of rotation and the visual target. The relative location of the center of rotation of the eye with respect to the head mounted head tracker receiver varies for each subject because of anatomical considerations.

Eye tracking and/or measurement can be done in many ways including: using a contact lens eye tracking method; using a head worn device for eye tracking and/or measurement; using a remote system; using a video camera, using a portable smart phone or other portable device, using a computing pad, using smart watch, attaching a sensor to another part of the body, and/or using a mobile or hand held pc computer. Eye tracking and/or measurement can be done: (a) in a non-contact fashion with the use of a light source (invisible light, such as with the use of an infra-red camera or light, or visible light), video camera or other sensor system designed to visually capture and record the eye movement activity; (b) with a marker or sensor on a contact lens; or (c) with a magnetic system using magnetized contacts and an external detector.

If a light source is used for eye tracking and/or measurement, the light source is directed toward the eye or eyes and a camera tracks the reflection of the light source and visible ocular features such as the pupil features and/or cornea surface reflection(s). The information can then be analyzed to extract eye rotation and ultimately the direction of gaze from changes in reflections. Additional information such as blink frequency and changes in pupil diameter can also be detected by the eye tracker. The aggregated data can be stored and written to a file that is compatible with eye-tracking analysis software. Graphics can be generated to visualize such findings. Beyond the analysis of visual attention, stored eye data can be examined to measure the cognitive state or other information.

A camera can be used as a sensor for detecting light in high resolution. When tracking and/or measuring the eye activity or eye movement, such as the VOR, an IR or video camera may be used and can be comprised of a single camera system or a multiple camera system. The camera can be located on the framework of the head worn device or within the lens material, or in the contacts being worn. If using a hand held device, the video camera can be located remotely in the device being held, mounted or worn elsewhere on the body. The camera control unit can be activated by such options as: an external wireless signal, a touch unit, rapid head movement or voice activation. The control unit can also be timer actuated, triggered by an eye blink for a defined period of time, or by placing the device on the head (e.g. putting on the head-worn unit). The eye tracking system can be mounted on a head worn device, on eyeglasses framework, or partially within the lens of eyeglass or contact lens on in a hand held mobile device, such as a smart phone, smart pad, or limb worn computer system.

The eye tracking and/or measuring system may include hardware such as an infrared camera and at least one infrared light source, a video tracking system and recorder. The infrared camera may be utilized by the eye tracking system to capture images of an eye of the wearer. The video images obtained by the infrared camera regarding the position of the eye of the wearer may help determine where the wearer may be looking within a field of view of the head mounted display used in the system. The infrared camera may include a visible light camera with sensing capabilities in the infrared wavelengths. Infrared light or radiation is a longer-wavelength radiation than visible light. It exists just outside of the spectrum of visible light. Heat, or thermal energy, is a common source of infrared light. An infrared camera is a device specially designed to detect and display the sources of this kind of light. A thermal infrared camera converts the heat detected into electrical signals, which are then projected in an image. Many types of night vision cameras are based on infrared light. A human body will always emit heat, and infrared cameras will detect this radiation.

The infrared light source can include one or more infrared light-emitting diodes or infrared laser diodes that may illuminate a viewing location, i.e. an eye of the wearer. Thus, one or both eyes of a wearer of the system may be illuminated by the infrared light source. The infrared light source may be positioned along an optical axis common to the infrared camera, and/or the infrared light source may be positioned elsewhere. The infrared light source may illuminate the viewing location continuously or may be turned on at discrete times.

The optical system may include components configured to provide images to a viewing location, i.e. an eye of the wearer. The components may include a display pane, a display light source, and optics, such as mirrors or refractive lenses. These components may be optically and/or electrically-coupled/connected to one another and may be configured to provide viewable images at a viewing location. One or two optical systems may be provided in the system. In other words, the head mounted display may allow the wearer to view images in one or both eyes, as provided by one or more optical systems. Also, the optical system(s) may include an opaque display and/or a see-through display connected to the display panel, which may allow a view of the real-world environment while providing superimposed virtual images. The infrared camera or video camera, using visible light, coupled to the eye tracking system may be integrated into the optical system with a data storage and logging recorder.

Video-based eye trackers typically use the corneal reflection (the first Purkinje image) and the center of the pupil as features to track over time. A more sensitive type of eye tracker, the dual-Purkinje eye tracker uses reflections from the front of the cornea (first Purkinje image) and the back of the lens (fourth Purkinje image) as features to track. A still more sensitive method of tracking is to image features from inside the eye, such as the retinal blood vessels, and follow these features as the eye rotates.

Eye tracking data can also be collected using a multicamera eye gaze tracker, which is based on one-camera gaze estimation algorithm. Using an algorithm, the 3D eyeball position can be estimated by the two corneal surface reflections (or glints) of the IR lights. Each camera can estimate the gaze independently and can allow large head movement. The accuracy of this system is less than 1 degree.

Eye tracking using binocular horizontal and vertical eye position estimates can be derived from the relative positions of multiple corneal reflections and the center of the pupil. By using two eye landmarks (corneal surface reflections and pupil center) whose relative position are invariant under translation, the angular position of the eye independently of lateral motion of the video system relative to the head is able to be estimated. The optical components can be mounted on an eyeglasses frame or goggles.

The light source can be infrared and can be directed toward the eye or eyes. The camera can be used to track the reflection of the light source and visible ocular features such as the pupil features, cornea reflection features or retinal data imaging. The collected data from the eye tracking system can be used to measure the movement features of the eyes or eyelids or rotation of the eye, acceleration/velocity of the eye movement, duration of the eyelid closure, rate of the eyelid closure and the direction of gaze. Additional information such as blink frequency and changes in pupil diameter can also be detected by the eye tracker. Aggregated eye tracker data can be written to a file for later analysis. Stored eye tracker data can be used to analyze the visual path across an interface such as a computer screen. In this case, each eye data observation is translated into a set of pixel coordinates. From there, the presence or absence of collected eye data points in different screen areas can be examined. This type of analysis is used to determine which features are seen, when a particular feature captures attention, how quickly the eye moves, what content is overlooked and virtually any other gaze-related data. Eye position is extracted from video images and graphics are often generated to visualize such findings. Search based on an electro-oculogram may be used. When using a video-based eye tracker, the camera can be focused on one or both eyes and used to record eye movement as a viewer looks at some kind of stimulus.

A thin prism can be used between the eye and a camera system, which acts as a light-guide altering the imaging path between the camera and the eye. The use of a thin prism can also provide on-axis illumination. This arrangement can enable an eyeglass like eye tracking device, which captures a frontal (i.e., on-axis) or near frontal image of the eye to have a visually appealing form factor.

In other embodiment multiple prisms can be used which can use a corrective optical element to eliminate any deviation or aberrations in the see-though viewing path, such that a user of the device can comfortably see through the eye-tracker normally. For example, in one of it aspects, the invention may include a wedge prism having only planar surfaces. This prism acts as a light guide to supply illumination light to the eye, as well as providing imaging light to the camera from the illuminated eye. In this embodiment a complementary prism can be arranged with respect to the thin prism such that the two prisms appear to the eye as a plane-parallel plate, or as a weakly powered optic.

In an alternative embodiment, an eye-tracker can use a free-form prism between the eye and a sensor. The freeform prism includes one or more surfaces with optical power, which are used both for imaging of the eye onto the sensor, and for optical aberration control. In certain embodiments, the freeform prism is used in conjunction with, or exclusive of, additional focusing optics such as a camera outside of the prism.

The eye imaging camera can be mounted on the arm of an eyeglass frame or on the framework around the lens and can capture the image of the eye through reflection off of the lens. In order to properly capture the eye image through reflection off of lens, there must be sufficient clearance between the user's face and the lens surface to avoid the obstruction of the eye image by user's face or the imaging optics.

Alternatively, the camera can be mounted on the glass frame under or over the eye, and directly image the eye. This requires a more robust frame design, which must move the camera far enough away from the face to avoid interference. In this system, the camera captures an eye image at a close distance and from a slanted direction (i.e., at an angle), which results the eye image suffering keystone distortion. This arrangement also presents optical performance challenges due to the large depth of field necessary to accommodate all possible eye positions.

A beam splitter in an eyeglass lens can be used, off of which an eye is imaged by a camera positioned out of a user's line of sight. A beam splitter is an optical device that separates a beam of light into two or more different beams of light. Beam splitters are available in various forms. These include cubes, pipes and plates. What happens with a beam splitter is that it accepts the input beam and then proceeds to divide the light depending on the specified requirements. The input beam could be polarized or non-polarized light. The most commonly used is the cube beam splitter although the plate beam splitter is typically used to produce lower cost non-polarized beam splitters. These typically provide a 50-50% split ratio. The reflected and transmitted light emerging from the beam splitters are at various angles, which often necessitates external mirrors to redirect the light. Embodiments of the present invention are directed to single prism beam splitters and compound beam splitters formed from combining one or more of the single prism beam splitters. The beam splitters can be configured to produce one or more split beams of light that emerge from the prism at angles other than 90° to one another. The prisms can be configured so that light propagating through prisms encounter one or more intermediate planar surfaces at various angles with respect to the path of the light. A certain number of the intermediate planar surfaces can be angled so that the light transmitted along a particular path undergoes total internal reflection ("TIR") at these intermediate planar surfaces. A number of other intermediate planar surfaces can be positioned or angled so that the light transmitted along a particular path does not undergo TIR. As a result, one or more beams of light propagating through the prism can be selectively split off to emerge from the prism by selectively disposing fully reflective and partial mirrors on the intermediate planar surfaces where TIR does not take place. The coating layer of a beam splitter can be made in such a way that a percentage of the light entering the beam splitter through one side can be reflected while another percentage is transmitted.

In other embodiments of the present invention, two or more of the single prism beam splitters can be combined to form compound beam splitters that split a single beam of light into three or more different beams of light. A beam splitter can have an optical multi-layer thin film, formed by laminating numerous layers in sequence. The numerous laminated layers can each be comprised of having a different refractive index.

In another embodiment, the eye tracking system can include a camera visor that is positioned in front of the eye of a user. In another embodiment, an array of optical detection elements can be placed directly onto the surface of the eyeglass-like lens located in front of an eye.

When using an eye-tracking camera, two general types of eye tracking techniques can be used: Bright Pupil and Dark Pupil. The difference between these eye-tracking techniques is based on the location of the illumination source with respect to the optics. If the illumination is coaxial with the optical path, then the eye acts as a retro-reflector as the light reflects off the retina creating a bright pupil effect similar to red eye. If the illumination source is offset from the optical path, then the pupil appears dark because the retro-reflection from the retina is directed away from the camera. Bright Pupil tracking creates greater iris/pupil contrast allowing for more robust eye tracking with all iris pigmentation and greatly reduces interference caused by eyelashes and other obscuring features. It also allows for tracking in lighting conditions ranging from total darkness to very bright. But bright pupil techniques are not effective for tracking outdoors as extraneous IR sources interfere with monitoring. In embodiments of the present invention, eye tracking might typically use a sampling rate minimally of 20 Hz. Typical sampling frequencies can include 20/30/50/60 Hz, 240 Hz, 350 Hz, and 1000/1250 Hz. The higher sampling frequencies are needed to capture the detail of the very rapid eye movement during reading, or during studies of neurology.

Embodiments of the eye tracking system can track on the cornea or further in the eye, based on using light reflected by the eye. Whether using an external source or ambient light, some of the techniques for tracking the eye include: limbus tracking, pupil tracking, Purkinje image tracking, corneal and pupil reflection relationship, corneal reflection and eye image using an artificial neural network.

Regarding limbus tracking, the limbus is the boundary between the white sclera and the dark iris of the eye. Because the sclera is (normally) white and the iris is darker, this boundary can easily be optically detected and tracked. The limbus tracking technique is based on the position and shape of the limbus relative to the head. This means that either the head must be held still or the apparatus must be fixed to the user's head. Due to the occasional covering of the top and bottom of the limbus by the eyelids, it is more helpful for precise horizontal tracking only.

Regarding pupil tracking, this technique is similar to limbus tracking. The difference is that in pupil tracking the smaller boundary between the pupil and the iris is used instead of the boundary between the white sclera and the dark iris. Once again, the apparatus must be held completely still in relation to the head. The advantages of this technique over limbus tracking is that the pupil is far less covered by the eyelids than the limbus, and thus vertical tracking can be accomplished in more cases. Also, the border of the pupil is often sharper than that of the limbus, which yields a higher resolution. The disadvantage pupil tracking is that the difference in contrast is lower between the pupil and iris than between the iris and sclera, thus making border detection more difficult.

Regarding Purkinje image tracking, when (infrared) light is shone into the user's eye, several reflections occur on the boundaries of the lens and cornea. These reflections are called Purkinje images. The first Purkinje image is also called the glint, and this together with the reflection of light off the retina, the so-called bright-eye, can be video-recorded using an infrared sensitive camera as a very bright spot and a less bright disc, respectively. When the eye is panned horizontally or vertically, the relative positioning of the glint and the center of the bright-eye change accordingly, and the direction of gaze can be calculated from these relative positions. The problems associated with this technique are primarily those of getting a good view of the eye; lateral head movement can put the video image of the eye out of focus, or even make the image of the eye fall out of view of the camera. Due to the lack of contrast, the center of the iris can be tracked instead of the center of the pupil Regarding pupil and pupil reflection relationship tracking, eye trackers can combine a camera with an infra-red light source that illuminates the eye with bursts of invisible infra-red light. Some of this infra-red light disappears into the pupil (the dark opening in the center of the iris), and some of it bounces back off the iris (the colored part of the eye), the cornea (the clear part at the front of the eye), the eyelid or the surrounding skin. All these different areas reflect different amounts of infra-red light, which is picked up by the camera. By analyzing the reflections using "a lot of very fancy matrix math" it is then possible to work out where the eye is pointing. Because eyes move in tandem, this only needs to be done for one eye. The technique is able to cope with blinking, head movements, dim light, glasses and contact lenses.

Regarding the use of artificial neural networks (ANNs) for computation, this is of the more recently developed techniques. The raw material for eye-gaze tracking is still a digitized video image of the user, but this technique is based on a more wide-angled image of the user, so that the entire head is in the field of view of the camera. A stationary light is placed in front of the user, and the system starts by finding the right eye of the user by searching the video image for the reflection of this light—the glint, distinguished by being a small, very bright point surrounded by a darker region. It then extracts a smaller, rectangular part of the video image (typically only 40 by 15 pixels) centered at the glint, and feeds this to an ANN. The output of the ANN is a set of display coordinates. The ANN requires more than the simple calibration that is required by the other techniques; it must be trained by gathering images of the user's eye and head for at least three minutes while the user visually tracks a moving cursor on the display. This is followed by an automatic training session that uses the stored images lasting approximately 30 minutes using the current technology, but then the system should not require re-calibration on the next encounter. To improve the accuracy of an ANN-based system, the corneal/pupil based calculations can be augmented with a calculation based on the position of the glint in the eye socket. The great advantage of ANN-based techniques is that due to the wide angle of the base image, user head mobility is increased.

Eye movement information from the eye tracker can be typically divided into fixations and saccades, when the eye gaze pauses in a certain position, and when it moves to another position, respectively. The resulting series of fixations and saccades can be called a called a scan path. Most information from the eye can be made available during a fixation, but not during a saccade. The central one or two degrees of the visual angle (the fovea) can provide the bulk of visual information; the input from larger eccentricities (the periphery) is typically less informative and analysis algorithms can be structured accordingly. Hence, the locations of fixations along a scan path show what information loci on the stimulus are processed during an eye tracking session.

Scan paths are useful for analyzing cognitive intent, interest, and salience. Other biological factors (some as simple as gender) may affect the scan path as well. As a participant looks at a page on the internet, the eye-tracking device can focus on the pupil of the participant's eye and determine the direction and concentration of the participant's gaze. Heat maps represent where the visitor concentrated their gaze and how long they gazed at a given point. Generally, a color scale moving from blue to red indicates the duration of focus. Thus, a red spot over an area of your page might indicate that a participant, or group of participants, focused on this part of a page for a longer time. Saccade pathways trace the eye's movement between areas of focus. The movement is not unlike watching a hummingbird move between flowers—there are periods of attention and then rapid movement. A red circle may indicate the area of focus, while a red line indicates the flight.

Another capability of the eye tracking technology is eye movement analysis, which can provide valuable insight into users' overt visual behavior and attention. The most common method for determining the location of a user's observable visual attention is by identifying the fixations and saccades that best indicate where they are focusing on the stimulus in front of them.

A linear filter may be used when processing eye-tracking data to approximate eye movement signals, at least well enough to recognize a pattern. The salient eye movements that are typically identified by eye movement analysis are fixations, saccades, and smooth pursuits. Fixations are a result of one's desire to maintain gaze on a specific, stationary object. Smooth pursuits are similar except for the object of interest is in motion. Saccades represent a voluntary shift of focus from one fixation point to another.

Saccades can be detected by two means as well: the position variance method and the velocity detection method. The position variance method identifies saccades as those moments in the signal in which the position of the eye changes rapidly. The velocity detection method uses an empirically determined velocity threshold. If the velocity of the signal is calculated as higher than the threshold, it is a saccade. Similarly, if it is below the threshold (as discussed above) it is a fixation. For both fixations and saccades, the velocity method is becoming more widely used because it is more suitable for real-time applications.

Beyond the analysis of visual attention, eye data can be examined to measure the cognitive state and workload of a person. Some techniques have been validated in multiple contexts as a reliable indicator of mental effort. Driving a car, reading a magazine, surfing the internet, searching the aisles of a grocery store, playing a video game, watching a movie or looking at pictures on your mobile device are such applications of eye tracking. With very few exceptions, anything with a visual component can be eye tracked. People use their eyes almost constantly, and understanding how the eyes are used has become an extremely important consideration.

In another embodiment the use of sensors on a contact lens can also be used for eye tracking eye responses and specifically VOR measurement. Employing multiple sensors on a contact lens can be used for detecting eye movement and contact lens orientation. They may also employ the use of markers or be magnetized. A multi-sensor contact lens can be placed in one or both eyes of a user and can actively determine movement activities of the eye. These sensors can be located on the surface of the lens or within the lens material. In another embodiment, an eye blink for a defined time can trigger the measurement of eye movement or turn on the device to begin the calibration for measurement. It is to be appreciated that both eyes of a human user generally blink at the same time, and thus in various embodiments only one multi-sensor contact lens is needed to generate a command to a remote device. Components on or within a contact lens can be of a shape, size, opacity, and/or positioned so as not to obstruct vision through an opening of a pupil of an eye when worn. Control features of multi-sensor contact lens can include issuing commands, adjusting content presentation, activating or deactivating options or components, or any other suitable functions. The multi-sensor contact lens can include either on or within its substrate a control circuit that can be coupled wirelessly to the multiple sensors.

In another embodiment, the multi-sensor contact lens can also communicate via a wireless network to a remote device. The remote portable device can include a wearable device, such as a head worn device or smart watch, or a non-wearable device, such as a remote mobile computer device, like that of a mobile smart phone, smart pad, pc and the like. The multi-sensor contact lens can use various kinds of sensors and they can be integrated in various combinations. The power component can include any suitable power source that can manage, receive, generate, store, and/or distribute necessary electrical power for the operation of various components of multi-sensor contact lenses. For example, the power component can include but is not limited to a battery, a capacitor, a solar power source, radio frequency power source, electrochemical power source, temperature power source, or mechanically derived power source (e.g., MEMs system). In another example, the power component receives or generates power from one or more of the sensors. A transceiver can transmit and receive information to and from, or within multi-sensor contact lens. In some embodiments, the transceiver can include an RF antenna.

3. Image Projection

Eye tracking and specifically VOR measurement can be performed using a virtual retinal display or holograph imaging in another embodiment. A virtual retinal display (VRD), also known as a retinal scan display (RSD) or retinal projector (RP), is a display technology that draws a raster display, or bitmap, directly onto the retina of the eye. The user sees what appears to be a conventional display floating in space in front of them. However, the portion of the visual area where imagery appears must still intersect with optical elements of the display system. It is not possible to display an image over a solid angle from a point source unless the projection system can bypass the lenses within the eye. In a conventional display a real image is produced. The real image is either viewed directly or, as in the case with most head-mounted displays, projected through an optical system and the resulting virtual image is viewed. The projection moves the virtual image to a distance that allows the eye to focus comfortably. No real image is ever produced with the VRD. Rather, an image is formed directly on the retina of the user's eye. Eye movement and head inertial tracking can be measured while being connected to a virtual display system. The measurements can also be triggered with an external "micro-controller". Not only can VOR testing and DVA measurement be done with the virtual display, but it can also be used for other "immersive testing", sport training, military training, commercial medical education or teaching.

Therefore, in an alternate embodiment, the camera can track the eye movement and measure the VOR using holographs or augmented reality display imaging.

Although the VRD is an output device, the technology lends itself to augmentation with eye tracking or eye gaze systems for input. The VRD system scanning light into only one eye allows images to be laid over one's view of real objects. The VRD system also can show an image in each eye with an enough angle difference to simulate three-dimensional scenes with high fidelity. The eye tracking can enable the fovea on the retina to always maintain good focus ability and as the pupil changes position, eye tracking with movement of the eye follows. As the eyes move, the foveation point can also change to achieve better tracking. Using a refractive lens can be used to prevent distortion of eye tracking. The fovea centralis, also generally known as the fovea is a part of the eye, located in the center of the macula region of the retina. The fovea is responsible for sharp central vision (also called foveal vision), which is necessary in humans for activities where visual detail is of primary importance.

In another embodiment low-persistence-of-vision display can enable a user to see images at only 24 frames per second. Even though the images flash by one by one, the mind fill in the blanks and the user will see (relatively) smooth motion. By reducing the amount of information the user sees, the brain can smooth out virtual reality. A head attached 6 DoF head tracker, with an adjustable sample rate, but minimally 20 Hz, and with tracker latency can be used to enhance virtual reality's realism on response time. Using a combination of 3-axis gyros, accelerometers, and magnetometers, can make it capable of absolute (relative to earth) head orientation tracking without drift. Each display to the eye can be adjusted with interchangeable lenses that allow for dioptric correction and adjustments for inter-pupillary distance requirements can be done. The mounted head tracker, when used with the eye worn virtual display can move the images to match the user's head movements, and create a greater sense of being inside a high definition LCD, LED or 1080p OLED 3D (3 dimensional) images being displayed. A wireless interface can be used for sending the collected tracking data to a remote device. Hand held micro-controllers can also be used to manipulate the displayed images and obtain more of an immersive testing, training or rehabilitation experience.

In another embodiment, a different medium platform can be used to project the visual data for measurement of the VOR, using a 3D (3 dimensional) virtual retinal display. In this embodiment, the virtual projection imaging device has no screen but can project images directly to the user's eyes. This screen-less display with the image displayed directly to the retina can also use a multiple micro-mirror design and low power light source. The image display quality can display a separate WXGA resolution (1,280×768) image directly onto the retina of each eye. The displayed images can be generated with reflected rather than emitted light. While LCD and OLED panels are emissive light, this display can project reflective light directly into the eye and mimicking more natural vision. The resolution and frame rate (minimally 240 frames/sec) can be high. Each eye can be focused independently focus and adjustments can be made to acquire a single image when wearing the device. Head inertial tracking and eye tracking can be incorporated in the head worn device. Two discrete images can be projected directly onto the retinas of the user and the optical elements can be individually adjusted.

To create an image with the VRD a photon source (or three sources in the case of a color display) can also be used to generate a coherent beam of light. The use of a coherent source (such as a laser diode) can allow the system to draw a diffraction-limited spot on the retina. The light beam can be intensity modulated to match the intensity of the image being rendered. The modulation can be accomplished after the beam is generated. If the source has enough modulation bandwidth, as in the case of a laser diode, the source can be modulated directly.

The resulting modulated beam is then scanned to place each image point, or pixel, at the proper position on the retina. A variety of scan patterns are possible. The scanner could be used in a calligraphic (vector) mode, in which the lines that form the image are drawn directly, or in a raster mode, much like standard computer monitors or television. Use of the raster method of image scanning allows the VRD to be driven by standard video sources. To draw the raster, a horizontal scanner moves the beam to draw a row of pixels. The vertical scanner then moves the beam to the next line where another row of pixels is drawn.

After scanning, the optical beam must be properly projected into the eye. The goal is for the exit pupil of the VRD to be coplanar with the entrance pupil of the eye. The lens and cornea of the eye will then focus the beam on the retina, forming a spot. The position on the retina where the eye focuses the spot is determined by the angle at which light enters the eye. This angle is determined by the scanners and is continually varying in a raster pattern. The brightness of the focused spot is determined by the intensity modulation of the light beam. The intensity modulated moving spot, focused through the eye, draws an image on the retina. The eye's persistence allows the image to appear continuous and stable. Finally, the drive electronics synchronize the scanners and intensity modulator with the incoming video signal in such a manner that a stable image is formed.

Liquid crystal displays (LCDs) currently are often used in display devices for the presentation of information. Particularly LCDs with 1080p HD can provide very good display quality and can be used in virtual reality display systems. An image that is generated electronically is viewed with the optical system of the eye. The image seen is subject not only to the quality of the optical system of the eye, but also to the quality of the display and the environment in which the display is located.

With a VRD, defects in the eye's optical system, such as damaged cornea and lens and reduced retinal sensitivity could be bypassed, as well as the problems of the display environment, such as ambient brightness, angle-of-view and display brightness. Additionally, the seen image could be augmented with other information and brightness of the system does not affect the image formed on the retina. It is believed that VRD based Laser or LED displays are not harmful to the human eye, as they are of a far lower intensity than those that are deemed hazardous to vision, the beam is spread over a greater surface area, and does not rest on a single point for an extended time. Optical damage caused by lasers comes from its tendency to concentrate its power in a very narrow area. This problem is overcome in VRD systems as they are scanned, constantly shifting from point to point with the beams focus. If the laser stops scanning, permanent damage to the eye will result because the beam stays focused in one spot. This can be prevented by an emergency safety system to detect the situation and shut it off. Apart from the advantages mentioned before, the VRD system scanning light into only one eye allows images to be laid over one's view of real objects. For example, it could project an animated, X-ray-like image of a car's engine or the human body.

VRD system also can show an image in each eye with an enough angle difference to simulate three-dimensional scenes with high fidelity. VRD can refocus dynamically to simulate near and distant objects with a far superior level of realism. VRD also supports proximity sensing. This means it can provide the illusion of being able to actually be more closely involved with the projected images.

In another embodiment a virtual-image projector can also be comprised of a laser configured to form a narrow beam, multiple other optics, and a controller. The multiple optics each have a diffraction grating. One optic can be arranged to receive the narrow laser beam and to project a one-dimensionally dilated beam into the second optic. The second dilation optic can be arranged to receive the one-dimensionally dilated beam and to project a two-dimensionally dilated beam, which the can provide a virtual image. The first and second redirection optics are each operatively coupled to a transducer. The video-display eyewear can resemble eyeglasses and can include a pair of projectors that project virtual display images for view by a wearer. The virtual display images are projected directly in front of the wearer's eyes. The device can include a wearable mount configured to position the projectors a short distance in front of the wearer's eyes. The device can also include controller, which controls the internal componentry of the projectors in order to form the virtual display images. Projectors may project virtual display images of infinitely distant objects, where the lens of the human eye adjusts to an infinite or near-infinite focal length to focus on such objects. The projectors may be at least partly transparent, so that the wearer can see external objects as well as the virtual display images. The glasses include lenses arranged in front of the projectors and they can be arranged in front of the projectors. The lenses may be configured to correct the focus and/or brightness of the external objects for the comfort and vision needs of the wearer. This arrangement may allow the wearer to shift his or her focus between the external objects, a finite distance away, and virtual display images an infinite distance away.

In an alternative embodiment, the controller can the cause projectors to project the same virtual display image concurrently, so that the wearer's right and left eyes receive the same image at the same time. In another embodiment, the projectors may project slightly different images concurrently, so that the wearer perceives a 3 D stereoscopic image.

In another embodiment, eye movement is measured without a camera system and utilizes electrodes placed on the surface of the skin around the eye(s). It is based on the principal where the eye acts like a battery: the cornea is the positive pole and the retina is the negative pole. Electrodes located in specific peri-orbital areas (e.g. around the eye) pick up the corneal-retinal electrical potential variation caused by eye movements, which are then amplified and sent to a recording device. Two (2) or three (3) channel recording devices can be used to record eye movements. An active electrode is placed next to the external corner of each eye and the third electrode is placed on the frontal midline in such a way that the three recording channels are configured as an isosceles triangle. Three bipolar derivations are set from the active electrodes, thereby making it possible to identify horizontal, vertical and oblique eye movements. Measuring the slow component velocity of nystagmus takes into account the directional influence of responses according to the vector projection of eye movements.

4. Head Tracking

Head tracking can be done using an Inertial Measurement Unit (also called an IMU or 'tracker'), which is an electronic device that measures and reports velocity, orientation, and gravitational forces, using a combination of sensors (accelerometers, gyroscopes and magnetometers). Unfortunately in practice IMUs can only accurately measure and report orientation values, not translations. Generally there are only 6 DOF in total, and can be divided into 2 different types, translations and rotations: A body is free to translate in 3 degrees of freedom: forward and back, up and down, left and right. A body can also rotate with 3 degrees of freedom: pitch, yaw, and roll.

Positional tracking is a mix of hardware and software which is able to detect the absolute position of an object. A MEMS gyro and a MEMS accelerometer are complementary sensors and are used together to measure 6-axis or "6 degrees of freedom" of motion processing supporting the full range of motion in a three-dimensional space. An accelerometer can measure linear movements and tilt, but because they cannot measure all rotational movements. In combination, the two sensors complement each other with the gyro providing turning information and the accelerometer providing rotation information. Motion processing tracks up to six degrees of freedom in free space and a motion-tracking device can combine sensor redundancy.

The head tracking inertial system can be mounted to the head in numerous portable embodiments, for example: at the top of the head with helmets, caps, straps or other head worn covering, in the center of eyeglasses, at the nose piece, in the side of the eyeglasses, in the ear or attached to the ear, or attached to the teeth with mouth guards, prosthetic attachments, or fixation with other oral appliances. In other embodiments the head tracking can be done from sensors in a hand held smart phone, smart pad, or other sensor system attached to a body part.

5. Fourier Analysis of VOR in a Natural Environment

A Fourier transform can be used to convert the relationship between an input (such as head motion) and an output (such as eye movement) in the time domain to a relationship in the frequency domain. By doing this, the VOR can be measured for natural motion in a non-clinical environment. As described previously, one of the traditional ways of measuring VOR has been to oscillate a subject's head at a fixed frequency and then to measure how quickly the eyes respond. For this kind of testing, a frequency of 0.5 Hertz would correspond to one cycle every 2 seconds. A cycle corresponds to the combination of one movement to the right and one movement to the left. These movements are typically in the form of a sine wave. The gain at this frequency would be the amount of compensation that the eyes make to the movement of the head. A gain of −1 (also often written as a gain of 1) is perfect because the eyes have rotated exactly the same angle as the head, but in the opposite direction. A gain of −0.75 (often written as 0.75) means that the eyes only compensated for 75% of the head rotation. The phase or phase lag describes how much later the eyes moved than the head. A phase or phase lag of 0 would mean the eyes followed exactly. A phase or phase lag of 45 degrees at a frequency of 0.5 Hertz means that the eyes were delayed by $\frac{1}{8}^{th}$ of 2 seconds (or 250 milliseconds) because 45 degrees corresponds to $\frac{1}{8}^{th}$ of a full 360-degree cycle. To determine gain and phase at a variety of frequencies using the traditional approach of oscillating the head in a clinical environment one would repeat the above test at a variety of frequencies and record the results. This method requires control over each input frequency and measuring the gain and phase of the eye response separately for each frequency, which will not work in a non-clinical setting having natural motion.

Any time-varying signal (such as the natural motion of an object in one dimension) can be converted to a series of sine waves. This conversion from a time-varying signal to a series of sine waves is called a Fourier transform. Fourier transforms can be discrete or continuous. A continuous Fourier transform is one in which the time-varying signal is converted to an entire range of frequencies with no gaps between the frequencies. A discrete Fourier transform is one in which the time-varying signal is converted to a specific set of frequencies, such as the series 0.125 Hz, 0.25 Hz, 0.5 Hz, 1.0 Hz, and 2.0 Hz. Discrete Fourier transforms are easier to calculate using digital electronics. By converting the observed natural yaw of the head as a function of time using a Fourier transform, one can generate a graph showing the amplitude of the input signal that the eyes would need to compensate for in order to follow a stationary image. By converting the sensed horizontal movement of the eyes at this same time using a Fourier transform, one can generate a second graph showing the amplitude of the eye signal that compensates for the head movement. By comparing these two graphs mathematically it is possible to determine gain at various frequencies directly from the natural head yaw movement. Similar mathematical calculations can be made to determine phase. The same method can be used to determine gain and phase in other dimensions such as pitch of the head versus the sensed vertical movement of the eyes, etc. Discrete Fourier transform calculations of this type can be performed by a microprocessor that receives the time-varying orientation signals from a head orientation sensor and the time-varying signals from an eye orientation sensor using mathematical calculations capable of being understood by anyone skilled in the art.

6. Other Potential System Elements

An example of a portable and wearable computing and head mounted display system can include an eye tracking and measuring system, a connected head mounted display tracking and measuring system, an optical system, peripherals, a power supply, a microprocessor, a memory, and a user interface. Components of the system may be configured to work in an interconnected fashion with each other and/or with other components coupled to respective systems. For example, the power supply may provide power to all the components of the system. The processor may receive information from and control the eye tracking system; the head mounted tracking system, the optical system, and peripherals. The processor may be configured to execute program instructions stored in the memory unit and to generate a display of images on the user interface. The display to the user can be presented as a 2D or 3D (3 dimensional) virtual display.

The system may include or be coupled to peripherals, such as a wireless communication interface, a touchpad, an integrated microphone, an high definition (HD) camera, and a speaker. Wireless communication interface may use 3G cellular communications, such as CDMA, EVDO, GSM/GPRS, or 4G cellular communications, such as WiMAX or LTE. Alternatively, wireless communication interface may communicate with a wireless local area network (WLAN), for example, using Wi-Fi. In some examples, wireless communication interface may communicate directly with a device, for example, using an infrared link, Bluetooth, near field communication, or ZigBee. In addition, other wireless interface communication can be used with "off-the-grid" networks (such are FireChat) where there is not cellular phone service or no internet connection.

The power supply may provide power to various components in the system and may include, for example, a rechargeable lithium-ion battery, solar power, mechanical power or various other power supply materials and types known in the art.

The processor may execute instructions stored in a non-transitory computer readable medium, such as the memory, to control functions of the system. Thus, the processor in combination with instructions stored in the memory may function as a controller of the system. For example, the processor may control the wireless communication interface and various other components of the system. In other examples, the processor may include a plurality of computing devices that may serve to control individual components or subsystems of the system. The processor, in conjunction with the memory unit, may perform analysis of the images obtained by the infrared camera.

In addition, the memory unit may store data that may include a set of calibrated wearer eye pupil positions and a collection of past eye pupil positions. Thus, the memory may function as a database of information related to gaze direction. Calibrated wearer eye pupil positions may include, for instance, information regarding extents or range of an eye pupil movement (right/left and upwards/downwards), and relative position of eyes of the wearer with respect to the HMD. For example, a relative position of a center and corners of an HMD screen with respect to a gaze direction or a gaze angle of the eye pupil of the wearer may be stored. Also, locations or coordinates of starting and ending points, or waypoints, of a path of a moving object displayed on the HMD, or of a static path (e.g., semicircle, Z-shape etc.) may be stored on the memory unit.

The system may include the user interface for providing information to the wearer or receiving input from the wearer. The user interface may be associated with displayed images, a touchpad, a keypad, buttons, a microphone, and/or other peripheral input devices. The processor may control functions of the system based on input received through the user interface.

One or more of the described functions or components of the system may be divided up into additional functional or physical components, or combined into fewer functional or physical components. For example, the infrared camera may be mounted on the wearer separate from the system. Thus, the system may be part of a portable/wearable computing device in the form of separate devices that can be worn on or carried by the wearer. Separate components that make up the wearable computing device may be communicatively coupled in either a wired or a wireless fashion. In some further examples, additional functional and/or physical components may be added.

The system may be configured as, for example, eyeglasses, goggles, a helmet, a hat, a visor, a headband, or in some other form that can be supported on or from a head or parts of the head of the wearer. The system may be further configured to display images to both eyes of the wearer. Alternatively, the system may display images to only one eye, either a left eye or a right eye.

If used as part of a head mounted display (HMD), the system may include a gyroscope, a global positioning system (GPS), magnetometer, and an accelerometer. The head mounted display tracking system may be configured to provide information associated with a position and an orientation of the HMD to the processor. The gyroscope may include a micro-electromechanical system (MEMS) gyroscope or a fiber optic gyroscope as examples. The gyroscope may be configured to provide orientation information to the processor. The GPS unit may include a receiver that obtains clock and other signals from GPS satellites and may be configured to provide real-time location information to the processor. The HMD-tracking system may further include an accelerometer configured to provide motion input data to the processor.

7. Additional Embodiments

In one embodiment, the device or method uses utilizes eyewear with an eye-tracking and measuring sensor, a head motion sensor and compares the gain and phase of each (e.g. an electronic circuit generates a comparison of the 3 axes from the head orientation sensing element with eye movement signals from the eye sensor to calculate a gain and phase of the eye movement response to head rotation, in the opposite direction). The eye orientation sensor senses vertical movement and horizontal movement of at least one eye. A visual target is provided in the eye worn lens, which can be otherwise transparent, translucent or opaque. The device or method can present this visual target to one eye (monocular) or both eyes (binocular). The device or method is sufficiently comfortable, secure to the head and lightweight to allow the user to have active head movements while wearing the device. Wearing such a mobile or portable, head worn or eye worn device requires a power source. If the power source is in the head worn device of the eye tracker or head tracker it can be rechargeable by a wireless interface.

The device can measure the relationship between motion of the head in this environment and VOR, DVA, DVS, and/or RIS. The data acquired can be uploaded to a remote position from the user for display and interpretation or transmitted wirelessly to a smart phone, wearable display device or other hand held device or other pc computer source. The eye tracker latency delay can be in the range 1 ms-10 ms and can have options to set the latency. The device can be charged with a wireless interface. The head orientation sensor does not use an external pulsed magnetic field and senses pitch and yaw of the person's head in a range of frequencies that comprises at least one frequency greater than 0.01 Hertz and less than 15 Hertz. The sensing of pitch and yaw can be accomplished using a micro-electro-mechanical system (MEMS) integrated circuit and roll can also be measured using such a circuit to provide three degrees of rotation information as well as three degrees of axial movement information for a total of six degrees of freedom. MEMS circuit can include any combination of accelerometers, magnetometers, and gyroscopes.

In one embodiment, a single camera system is used for the eye tracking. In another embodiment a multi-camera system is used and the cameras can be located in the lens, framework or eye or head worn device or located remotely. The camera control unit can be activated by such options as: a touch unit, rapid head movement, voice activation, timer actuated, an external wireless signal, or by placing the device on the head (e.g. putting on the head-worn unit). An eye blink, for a defined period of time, can also trigger the camera for measurement of the eye movement activity or VOR. An algorithm measuring blinking time and duration to determine involuntary eye blinks versus a voluntary eye blink can issue a command to the control circuit to operate the camera system. A micro-controller communicates with the system to support the commands. The camera system can be comprised minimally of a 5-megapixel camera capable of recording 720p to 1080p video built-in, a microphone for voice commands, and at least 12 GB of usable storage. It can support Bluetooth and Wi-Fi, and can works with an Android or iOS smartphone. The VGA resolution optical engine will provide at least a 25° field of view. This can also have an onboard OMAP processor running Android or iOS smartphone, embedded with a 9 DoF motion sensor. Providing direct image overlay over the wearer's main line-of-sigh, coupled with the motion sensors and camera, it can enable true augmented reality capability. The Android phone/smart phone, or smart pad can also serve as a wireless remote control.

In one embodiment the eye-tracker uses the center of the pupil and infrared and/or near-infrared non-collimated light to create corneal reflections (CR). The vector between the pupil center and the corneal reflections can be used to compute the point of regard on surface or the gaze direction.

In an alternative embodiment of a binocular system, two mirror-image optical systems are mounted on each side of the eyeglasses frame. The corneal reflections are generated by illumination with two infrared LED's mounted to the glasses frame. These LED's also serve to illuminate the pupil. The use of infrared (IR) light allows for invisible illumination of the eye. The use of multiple corneal reflections extends the linear range of the system by ensuring that one corneal reflection is always visible on the spherical surface of the cornea even with eccentric gaze. The images of the pupil and corneal reflections are reflected off of an IR mirror positioned in front of the subject's eye and directed to the cameras. This mirror is transparent to visible light and thus does not interfere with normal vision. The video image is sampled by a custom charge-coupled device (CCD) array that allows images to be sampled minimally at 20 Hz. Images from the CCD camera are processed in real time to obtain estimates of the corneal reflection and pupil center locations. Calibration of the eye tracker can be performed using a light source, such as a laser pointer, and calibration procedure looking at multiple objects or points (usually 5).

Another embodiment may use an OLED-based eyewear display which enables the eye tracking of a person with the use of an embedded IR display and camera in the see-through-lens of a head mounted/eye worn device. This can be worn as a monocular or binocular device with a transparent OLED display inside, which overlays digital information on top of the reflected light that strikes the eye. A bi-directional micro-display can be used in the head worn system for additional gaze triggered augmented-reality (AR) applications. The display contain both an active OLED matrix and integrated photodetectors that can track eye movement activity with front brightness up to 2000 cd/m².

Another embodiment can use a Liquid Crystal on Silicon (LCoS), field-sequential color, LED illuminated display. The display's LED illumination can be polarized and then shines through the in-coupling polarizing beam splitter (PBS) to the LCoS panel. The panel reflects the light and alters it to S-polarization at active pixel sites. The in-coupling PBS then reflects the S-polarized areas of light through the out-coupling beam splitter to a collimating reflector at the other end. Finally, the out-coupling beam reflects the collimated light into the wearer's eye.

In another embodiment a low persistence OLED (Organic Light Emitting Diode) 1080p HD 3D (3 dimensional) virtual display can be utilized for VOR measurement. The OLED display may not be as bright as an LCD display, but it has a major advantage in delivering crisp, rapid movement without any smearing or ghosting of objects. Multiple separate cameras or a single large screen, which is split in half, can be used to provide two view points for each half of the screen. The two views can then be seen separately to either eye to with lenses in the head worn device, to provide a wider field of view. Orientation and movement can be tracked with the stereo 3D (3-dimensional) head tracker with 360 degrees. The user when being tested with the 3D (3-dimensional) virtual display has a sense of being "intimately around the points of visual focal interest". An additional embodiment of using a hand held controller can also be used to sense motion anteriorly and posteriorly, with a 3D (3-dimensional) hand held mobile controller. Testing of the VOR can also be tested with pitch and roll of the head tilt. Predictive tracking (e.g. algorithm which can predict the next head position and orientation can help computing and updating) can be used to prevent latency issues and lessen motion disturbances while being tested. A bone conducting sensor incorporated in the framework can provide auditory/acoustic signals to the user. This data can then be stored, logged, interpreted and uploaded to a remote location.

The eye tracking system can be used with or without a light source. Therefore, another embodiment of eye gaze tracking can be provided with magnetized contact lenses tracked by magnetic sensors mounted on the user's eyewear and/or reflectors or markers on the contact lenses tracked by video-based sensors, also mounted on the user's eyewear. Tracking information of contact lenses from magnetic sensors and video-based sensors may be used to improve eye tracking and/or combined with other sensor data to improve accuracy of eye tracking. Contact lenses may be tracked by one or more mounted head worn cameras and/or magnetic sensors in order to resolve tracking information, such as position of the objects, the distance between the objects and a camera, and the like. Furthermore, reflective contact lenses improve blink detection while eye gaze tracking is otherwise unimpeded by magnetized contact lenses. Additionally, contact lenses may be adapted for viewing 3D (3-dimensional) information. Alternatively, another method could be to place four evenly spaced sensors on the inside of the contact lens, so they cover every angle of the eye movement. The sensors could even be embedded in the lens itself.

In further embodiments, magnetic sensors and video-based sensors may be used in combination to track a magnetized contact lens with one or more reflective patterns, provide blink detection, and eye movement. Other video-based sensors may be used to locate the head position of a user and prune noise from other magnetic or other light sources. Additionally, tracking information from contact lenses of both eyes may be used to improve accuracy.

Magnetized and reflective contact lenses may be utilized to browse menus of computer applications, control virtual characters of video games, select-drag-manipulate objects, and perform other trained or learned actions responsive to a user's eye movement or eye gaze. In further aspects, magnetized and reflective contact lenses can be used in any application that can benefit from eye and/or gaze tracking.

In one embodiment, magnetic sensors may be placed on a video game console or near the head of a user of a video game console to track the location and polarization of magnetized contact lenses. In another embodiment, video-based sensors may be used to track the location of reflective contact lenses transparent to normal light and reflecting one or more portions of the electromagnetic spectrum.

Contact lenses in embodiments can be passive (e.g., utilizing color or polarity for 3D viewing) or active, for example, using a liquid crystal layer that is normally transparent but darkens when a voltage is applied.

One of the advantages of using contact lenses for eye tracking and viewing 3D (3 dimensional) information is that they are more practical (i.e., smaller, light weight and easy to carry around) compared to some peripherals used for eye gaze tracking or for 3D information viewing. For example, glasses typically used for 3D information viewing or head-mounts typically used for eye gaze tracking can be complex and cumbersome.

In addition, contact lenses can offer highly accurate eye tracking information at low cost. For example, when contact lenses are used for eye gaze tracking, the performance can be better than the one that can be achieved with a camera-based eye tracking solution. Also, compared to camera-based solutions which require expensive high-resolution cameras, contact lenses can offer low cost solutions which make them more suitable for consumer products.

Accordingly, in various embodiments, a combination of marker-based and marker-less eye tracking techniques using contact lenses provide interacting with or controlling objects or menus of a video game, a projected visual user interface, an augmented virtual reality user interface, or the like.

In another embodiment contact lenses with embedded electronics inside such as LEDs, LCDs, or new nano-electronic materials can also be used for eye tracking. Applications of electronic contact lenses may be even more promising.

An inertial measurement unit (IMU), or 'tracker') is a small unit which houses a number of sensors used to get information about the position of the head in space. Adding a tracker to a head worn or eye worn device allows the position of the user's head to be tracked. Trackers constantly ping the sensors in the IMU to get information from them. The rate at which this happens is expressed as [samples] Hz (per second). Degrees of freedom describes the possible movements of an object. In reality there are only 6 degrees of freedom total, three of which come from rotation of an object (roll, pitch, yaw) and three which come from the translation of an object (forward/backward, left/right, up/down). All of these degrees of freedom can be quite accurately tracked with an accelerometer, magnetometer, and gyroscope. The wearer of a head tracker may perform a gesture to indicate an attempt to unlock the head mounted camera display. For example, a gyroscope coupled to the head mounted display may detect a head tilt, for example, and indicate that the wearer may be attempting to unlock the head mounted display screen.

In one embodiment the head tracker has 3 axis each of accelerometer, magnetometer, and gyroscope, an RGB LED, an 800-925 nm infrared LED, a battery and wireless interface charger, a wireless interfaced micro-controller, and a transceiver. The gyro is capable of sampling rates up to 760 Hz, and the transmitter link has the throughput to transmit that fully under 1 ms latency to the remote station. Full positional updates (fused information from all the sensors) from the IMU can be sent at a rate of at least 500 Hz. The head tracker is 6 DOF because it uses three sensors and can track roll, pitch yaw, as well as inertia when the unit moved forward/back, left/right, and up/down. The device can have redundant sensors for the same degree of freedom.

Another embodiment can use eyewear which has elements in the transparent, opaque or semi-transparent lens comprised of: calibration points, light source, camera for recording eye movements. In this embodiment no mirrors are utilized. The framework provides the power source, data logging capacity, software for measurement and can include: alarm signal for movement of the head, sensors to transmit collected data to remote source and data interpretation. This can be done with passive head movements or active head movements and an alarm in the device can trigger the timing event of head movement, rather than having another person move the user's head for more of an "active head movement test". Specifically the electronic circuit can be triggered or turned on by verbal command (auditory input), by visual means (such as prolonged eyelid closure or other specific eyelid movement), mechanically (such as by the attachment of the head worn device to the head), with timer software programming, and remotely. Additionally this worn device can provide software to detect a value or abnormality for eye response or eye reflex, where eye response (or reflex) might be VOR, DVA, DVS, or RIS. This eye response (or reflex) output could be reported as a binary (normal or abnormal) value or it could be reported as a score on a continuous scale, such as the way in which other physiologic parameters (such as height, weight, blood pressure, temperature, and many more parameters) are reported. If a score is reported, it could be a score for a single parameter at a single frequency, such as gain or phase at 0.5 Hertz, or it could be a multi-frequency composite score (such as gain or phase or a combination of gain and phase at a range of frequencies from 0.1 Hertz to 1 Hertz). The score could be for one eye or both eyes. The score could include measurement of asymmetry. An eye response (or reflex) score on a continuous scale or on a continuous composite scale (or a simple reporting of abnormalities), could then benefit from a rehabilitative VOR eye-tracking program. This can then enable the person to develop normal VOR again or enhanced eye fixation and specifically RIS on a target of interest with head rotation or head movement, or improve other ocular response or reflex capabilities while performing their occupational activities.

If the device does not need to be completely portable and self-contained, one can perform inertial head tracking with six degrees of freedom of head motion by using external signals to such as pulsed magnetic fields and a magnetic position transducer mounted to the eye-tracker goggle assembly. The transducer can be mounted on the eyewear/head for azimuth rotation. A fixed transmitting device can radiate a pulsed magnetic field in which the head mounted receiver is immersed. The field is sensed by the receiver and processed by a microprocessor to provide three-dimensional (3-D) position information as well as head elevation, azimuth and roll angles. The head tracker provides absolute angular and translational position measurements and does not require calibration for each person. The head tracker can operate with multiple receivers allowing for measurement of other important parameters such as hand position in hand-eye coordination studies. Other embodiments that use external signals can include the use of external infrared and ultrasonic signals to detect the position and orientation of the head or other part of the human anatomy.

In another embodiment the mounted head tracker sensor in the head worn/eye worn device includes a gyroscope, accelerometer, and magnetometer. The mounting of the head tracker can be in the center of the head worn device, or in the nosepiece with eyeglass device or on the sides of the eyeglasses. The head tracker can also be mounted to a removable in-the-mouth appliance, which is fixed to the tooth. It can also be incorporated into a mouth guard or retainer device. The mouth worn device can also generate a sound signal to produce imperceptible sound vibrations that are conducted via the teeth, through bone, to the cochlea and providing the user with signals to move the head. When the data from these devices is fused, the orientation of the head in the real world can be determined and synchronize the user's virtual perspective in real-time. The process of combining the sensor data from all three devices into something useful is called "sensor fusion." The gyroscope, which reports the rate of rotation (angular velocity) around X, Y and Z axes in radians/second, provides the most valuable data for head orientation tracking. By constantly accumulating angular velocity samples over time, the direction relative to where it began can be determined.

Another alternative embodiment of the invention is an inertial angular orientation tracking apparatus mounted to the head worn device. Drift sensitive sensors, such as angular rate sensors, produce a signal that is integrated to give a signal that represents angular position. The angular position signal may drift, due to integration of a bias or noise in the output of the rate sensors. To correct this drift, compensating sensors, such as gravimetric tilt sensors and sometimes also geomagnetic heading sensor(s) periodically measure the angular position, and this directly measured position signal is used to correct the drift of the integrated position signal. The direct angular position sensors cannot be used alone for dynamic applications because the gravitational sensors are also affected by non-gravitational accelerations, and therefore only accurately reflect angular position when under the influence of no non-gravitational accelerations. Typically, the drift sensitive sensors are angular rate sensors, (these include: rate gyroscopes and vibrating piezoelectric, magneto-hydrodynamic, optical and micro-machined silicon devices) the output from which are integrated once. However, other suitable drift sensitive sensors include linear accelerometers used to sense angular rate, gyroscopic angular position sensors and angular accelerometers. Typically the compensating sensors are inclinometers, accelerometers and compasses.

In another embodiment a head orientation and/or inertial tracking device can be used that is essentially "sourceless", in that it can be used anywhere with no set-up of a source, yet it enables a wider range of virtual environment-style navigation and interaction techniques than does a simple head-orientation tracker, including manual interaction with virtual objects. This device can feature a sourceless orientation tracker including an inertial sensor, a tilt-sensor, or a magnetic compass sensor.

In another embodiment, the device can include a position tracker which includes an acoustic position tracker, an electro-optical system that tracks LEDs, optical sensors or reflective marks, a video machine-vision device, a magnetic tracker with a magnetic source held in the hand and sensors integrated in the headset or vice versa, or a radio frequency position locating device.

In an alternative embodiment, the present invention not only measures the VOR or RIS with head movement, but also rehabilitates/retrains the user when an abnormality is present, to enhance the VOR and RIS or retinal visual accuracy with specific visual stimulation and head movements. This rehabilitation can be done for specific VOR pathologic findings. Specifically when there is an abnormal VOR in the horizontal plane, specific algorithms of eye fixation on a target object, while the head is moving horizontally can be used to rehabilitate the abnormality. When the abnormal VOR is seen in the vertical plane, specific algorithms of eye fixation on a target object, while the head is moving in a vertical manner can be used to rehabilitate the abnormality. As the VOR is enhanced or improved, the DVA or RIS will be enhanced.

In one embodiment, the device or method could provide a sound signal and/or visual signal to alert or trigger the user to respond by moving the eye or head. Remote sensing, see through capability with the head/eye worn device, and the rendering of a visible target in broad daylight are all features that can be incorporated in embodiments of the present technology. The head/eye worn device or method could also collect the data, which could then be uploaded to a medical doctor, trainer, coach or other person at a remote location. This remote location could then provide verbal or visual feedback to the user and this feedback could be integrated with other information provided to the user.

In one embodiment the device or method disclosed here can also be used to help a person improve his or her VOR and DVS and accuracy used during activities in daily living, routine exercise, and high level athletic/vocational activities. This can be used to help a person improve his or her balance by challenging, exercising, enhancing, and/or retraining the VOR (fixation/re-fixation) used during activities in daily living, routine exercise, and high level athletic/vocational activities and therefore improving the retinal visual stability and accuracy. Thus, embodiments of the present invention can incorporate head movements in one or a number of planes as part of a systematic program for enhancing the VOR and DVA. Using the devices and methods described here it is possible for rehabilitation programs to incorporate head movement with stable image identification and image identification movement with the head remaining stable. The data obtained from the devices and methods described here can be used for wireless communications. The data can be embedded GIS or geographic information system of the eyes or a digital map of where the eyes are located relative to the head movement.

An alternative embodiment can be the use of a general purpose portable, battery operated, hand held device, such as a smart phone, computer pad, or other wearable computer device which can be used for the VOR measurement. In this embodiment all of the elements in the head mounted device for measuring the VOR, RIS and VOR rehabilitation methods are in the hand held device including: the eye tracker (using IR, LED or other visible light source for illumination, or marker on contact lenses), a head tracker, software, auditory signals and visual display. In this alternative embodiment the user can look at the hand held device or body worn device, eye tracking and head tracking inertial measurements are obtained. Sensors record the eye movement as the head moves and the data is stored, logged, interpreted, displayed in the hand held device, and further stored or can be remotely transmitted. This can be done with passive head movements or active head movements and an alarm in the device can trigger the timing event of head movement, rather than having another person move the user's head for more of an "active head movement test. Additionally this portable hand held device or limb worn device can provide a software rehabilitative eye tracking program, if an abnormality is present. This can then enable the person to develop normal or enhanced eye or retinal fixation on a target of interest with head rotation or head movement, while performing their occupational activities. Additionally fiduciary markers can be applied on the head to facilitate inertial head tracking.

In one embodiment, the device can be calibrated before it is used to measure VOR. When used in the laboratory setting, calibration can be performed by focusing on a distant target, such as a light bar or laser light which is projected to the wall.

The image moves horizontally, vertically and then is center located. Typically, several trials are performed to establish good reproducible results. During this test, the patient is instructed to rotate the head from side to side horizontally or vertically to an auditory cue at frequencies ranging from 2 to 6 Hz. Eye movements are recorded including: direction, amplitude, and velocity of eye movements. Head inertial movements are recorded by the velocity rate sensor attached to the head. Tracking eye movement from spot to spot in this way is called "active tracking". When used in a non-laboratory or a non-clinical setting, similar testing can be performed if there are objects available that will serve the same purpose as the distant target in the laboratory setting. Testing of this type allows gain, phase, and asymmetry to be measured separately at each frequency. A more sophisticated approach would be to ask the subject to follow an object that is not necessarily moving at one specific frequency, but at a combination of frequencies and then using a Fourier transform to convolve the gain, phase, and asymmetry at various frequencies directly from the complex waveform that was being followed by the subject.

As described in the previous paragraph, in some embodiments of the present invention, the head movement tracked and measured can be active. Another approach is to use and measure natural movement that normally occurs during normal activities or activities associated with a person's work and to compare that to the eye movement that occurs at the same time through the use of a Fourier transform. This approach can be called "natural tracking" A third approach is to attach the head to something that then forces the head to move in a specific pattern—which is called "passive tracking."

In embodiments of the present invention, the head movement testing can be used to sense horizontal, vertical or torsional movements at various linear velocities, angular velocities, linear accelerations, angular accelerations, or frequencies. Natural test method testing in the horizontal plane could utilize focusing on a target moving across the horizontal visual field. Watching a moving object ascend and descend in the air would provide a vertical test in a natural manner.

Any combination of the discussed embodiments of head inertial trackers and eye tracking systems can be used to measure the ocular response (e.g. VOR) with head movement. If active tracking is used, the user visualizes a target of interest while moving the head. The target the user is focused on can be seen through a see-through lens (e.g. such as looking at a dot on a wall projected in front of them) or, if wearing other semi-transparent or non-transparent head worn applications (such as a pair of goggles), the target may be displayed as a 3D image, hologram or some other light source image. Video camera eye orientation tracking, using invisible or visible light, simultaneously can be used with head tracking. As the head moves, the ocular responses can be tracked and measured by a variety of modalities. A Fourier transform can be used to compares the inertial head movement and eye movement response at various frequencies in a complex waveform and software can analyze the data. The stored data can be displayed remotely and abnormalities of the related ocular response to the head movement can then predict the performance of the user when performing an occupational activity.

In the prior art, clinicians have looked at the VOR response and made a binary judgment (e.g. the VOR was abnormal or normal). This normal/abnormal criterion would then be used to determine whether vestibular rehabilitation was needed. A better method for evaluating the VOR response would be to VOR performance on a continuous scale, just like we measure the speed of an athlete. By doing this, one can get a subject's human performance measurement. Specifically there can be a VOR response score that more clearly establishes the vestibulo-ocular response measurement and expresses this response measurement in language that can more appropriately be applied to human performance measurement and improvement. Establishing such a scoring system will enable people to more accurately predict human performance with specific activities. It may also help in the development of activities that improve the human performance in fields where above average VOR is of benefit. The same use of scoring on a continuous scale and multi-frequency composite scoring can apply to DVA, DVS and RIS.

8. Areas of Application

There are many applications for measuring eye responses such as the VOR, DVA and DVS devices and methods here. For example, in sports, the technology described can predict play performance, position performance and it can also be used to help detect and/or assess concussions to determine whether a player can return to the sport after suffering a hit. Having an abnormal VOR or abnormal DVA can also be used in the pre-selection process for athletes, military personnel, pilot training, or in any other vocational selection process where a high level of human performance is required. The following paragraphs provide greater detail about the use of VOR, DVA and DVS using the embodiments previously described.

Athletics.

Embodiments of the present invention can be used in athletic environments where VOR can help predict performance and early detection of VOR abnormalities and DVA difficulties can be used to identify medical conditions that in a real time environment. Specifically if a player has an abnormal VOR/DVA in the horizontal plane, that person may not be able to catch a ball when competing in athletic activities that require the head to rotate in a horizontal plane. Similarly if a player has a vertical VOR/DVA abnormality and is running downfield while looking upwards over the shoulder, the ball will not be in focus. Specifically, the retinal visual stability and accuracy would be diminished. In this instance, there would a higher likelihood of dropping the ball compared to another athlete who has normal VOR responses with normal DVA. If there were a VOR abnormality, which would cause an abnormality of the RIS, seen prior to play, an athlete could do VOR retraining, in an attempt to rectify the abnormality and therefore improve play performance. Alternatively, the coaching staff could select another athlete who did not have this abnormality for specific task performance. VOR testing of athletes on the day of play and can predict the likely performance ability of that particular athlete when moving the head in a particular plane of rotation or translation while attempting to fixate on an object such as a ball. For example, on game day if a football player had an abnormal VOR, with resultant decline in the DVA, in the vertical plane (e.g. lack of visual fixation on an object of interest with upwards and downwards movement of the head), then it can be predicted that the athlete is predictable not likely to catch a ball while running downfield and looking upwards over the shoulder (e.g. you cannot catch, what you cannot accurately see). This would offer some value to the coaching staff in selecting plays for the player or players for the necessary play to be performed. Additionally, if an athlete had such an abnormality and could be given some rehabilitation methods prior to play, this could correct the abnormality and increase performance in that activity. Athletes who have had concussions can have a VOR abnormality, with resultant decrements in the DVA or RIS. Embodiments of the present invention can be an accurate method to determine when the athlete is ready to return to play activities, based on improvement of the VOR or DVA. It therefore can be utilized in concussion evaluation/assessment and concussion management for return to play. It is also intended for athletes who wish to enhance their training and athletic/vocational performance. It can be used in fitness centers, sports training centers, athletic performance centers, and vocational performance centers.

Military personnel functioning in a high-level environment and requiring target fixation of their eyes, while performing other activities such as with head or body movement, require a normal VOR and normal DVA. If the VOR/DVA is abnormal, the individual will not demonstrate peak human performance. Embodiments of the present invention can be used by the military in places such as the pilot selection process or special operations community to aid in the selection of individuals without a VOR/DVA abnormality. VOR/DVA measurement could enable other individuals, who had normal retinal visual stability and accuracy, to be chosen for a particular task that has better predictable performance for a particular duty of the day.

Medical.

Similarly any person with a motion sensitivity disorder (such as motion sickness, vection induced motion sickness, or visually induced motion sickness) or a balance problem, either of a central or peripheral origin, will have a VOR/DVA abnormality. Individuals with such an abnormality will express symptoms of dizziness, disorientation, difficulty with focusing, nausea, fuzziness, and such other complaints as not being clear headed. Embodiments of the present invention can be useful to people who have experienced a vestibular insult, vestibular dysfunction or labyrinthine dysfunction such as those caused by infection, concussive injury, traumatic brain injury, vascular disease, ototoxic or vestibulotoxic medication use, surgical complications, Meniere's disease, people experiencing chronic imbalance, such as, but not limited to, stroke victims, people with systemic illnesses, the elderly and other people who have experienced head injuries, especially those who have experienced cerebral or labyrinthine (inner ear) concussions. It can be used in physician offices to see if such a gaze stabilization accuracy problems exists and can be useful in the treatment of such an abnormality when it is present. It also can be utilized other centers which perform vestibular rehabilitation and athletic/vocational enhancement environments.

Commercial.

Embodiments of the present invention can also be used in other industries where individuals are expected to perform in high activity levels, which may often be also in provocative environments with head/body motion.

Vestibular Rehabilitation.

VOR scoring can also be beneficial in determining who is likely to benefit with vestibular rehabilitation therapy. VOR scoring can also be used more objectively in determining the benefit or improvement with such therapy. The system can include improvement information that can be used by the user, a coach, a medical practitioner, or any other advisor to help interpret the scoring and provide advice and/or exercises to improve ocular reflex. Although vestibular rehabilitation therapy can improve the ocular responses, this scoring can accurately quantify the improvement and more ably predict who is able to return to their normal activity without loss of human performance. Having a VOR score can also provide feedback that helps to control abnormal VOR responses.

When an ocular response is abnormal with head rotation (a VOR abnormality, for example), such a finding can also determine a need for improvement with rehabilitation. Repetitive head movement in the abnormal plane of rotation, while the eye remains fixed on a target of interest, can provide a means for improving or enhancing the VOR or other eye responses. Specifically, if a VOR abnormality is found to exist in the horizontal plane, VOR enhancement rehabilitation therapy is given in the same plane. In this instance, the user focuses on a target of interest and the user rotates the head horizontally, while continuing to look at the target. If a VOR abnormality is found to exist in the vertical plane, VOR enhancement rehabilitation therapy is also given in the similar plane of the abnormality. In this instance, the user focuses on a target of interest and the user rotates the head vertically, while continuing to look at the target. The head speed can be varied and the target, which the user is focused, can be changed. The process can be repeated as often as necessary until the VOR abnormality is corrected. This therapy can be performed in any plane where such an abnormality exists. The same use of scoring on a continuous scale and multi-frequency composite scoring can apply to DVA, DVS and RIS.

The present invention permits supernormal enhancement of these same systems where no balance disorder exists, as in the case for enhancement of athletic and vocational abilities. Such an enhancement methodology can be used in athletic/vocational enhancement or training and other training environments such as virtual reality training and the like.

While the disclosure has been described with respect to a limited number of embodiments and areas of use, those skilled in the art, having benefit of this disclosure, will appreciate that other embodiments may be devised which do not depart from the scope of the disclosure as disclosed herein. The disclosure has been described in detail, it should be understood that various changes, substitutions and alterations can be made hereto without departing from the spirit and scope of the disclosure.

What is claimed is:

1. A system comprising a portable ocular reflex measuring device wherein the portable device comprises:
    an eye orientation sensor wherein:
        the eye orientation sensor comprises a module selected from the group consisting of an image detector, a magnetic field detector, and an electrical potential detector; and
        the eye orientation sensor senses vertical movement and horizontal movement of at least one eye;
    a head orientation sensor wherein:
        the head orientation sensor is attachable to a person's head;
        the head orientation sensor senses pitch and yaw of the person's head wherein pitch represents a rotation about a first axis representing up and down movement of the person's face when the rear of the person's head moves in the opposite direction and yaw represents horizontal movement of the face when looked at from the front about a second axis substantially aligned with the spine and perpendicular to the first axis; and
        the head orientation sensor senses pitch and yaw in a range of frequencies between 0.01 Hertz and 15 Hertz;
        the head orientation sensor comprises a micro-electromechanical system integrated circuit comprising a module selected from the group consisting of an accelerometer, a magnetometer, and a gyroscope; and an electronic circuit wherein:
  the electronic circuit comprises a power supply, a communications unit, logic circuitry, a central processing unit, a memory unit; and sensor data pre-processing circuitry;
  the power supply comprises a battery;
  the electronic circuit is responsive to horizontal and vertical eye movement information received from the eye orientation sensor;
  the electronic circuit is responsive to pitch and yaw information received from the head orientation sensor;
  the communications unit is configured to transmit orientation information related to the eye movement information, the pitch information, and/or the yaw information;
  the electronic circuit uses a Fourier transform to generate a vertical gain signal and a vertical phase signal in response to the vertical eye movement information and the pitch information; and
  the electronic circuit uses a Fourier transform to generate a horizontal gain signal and a horizontal phase signal in response to the horizontal eye movement information and the yaw information.

2. The system of claim 1 wherein:
the system is designed for use in an ambulatory occupational environment outside of a medical facility;
the device measures a physiological condition selected from the group consisting of vestibulo-ocular reflex, dynamic visual acuity, dynamic visual stability, and retinal image stability;
the eye orientation sensor comprises an image detector;
the image detector comprises a video camera;
the video camera is responsive to motion of an eye feature selected from the group of the pupil, the cornea, the iris, the limbus, and the retina;
the eye orientation sensor senses movement of both the left eye and the right eye;
the eye orientation sensor senses rotational movement of at least one eye wherein the rotational movement represents a rotation of the eye as viewed by looking at the front of the eye;
the head orientation sensor senses roll of the person's head wherein roll represents a rotation about a third axis substantially orthogonal to the first axis and the second axis representing rotation of the person's face when viewed from the front;
the electronic circuit is responsive to both left eye movement information and right eye movement information received from the eye orientation sensor;
the electronic circuit is responsive to rotational eye movement information received from the eye orientation sensor;
the electronic circuit is responsive to roll information received from the head orientation sensor;
the electronic circuit uses a Fourier transform to generate a rotational gain signal and a rotational phase signal in response to the rotational eye movement information and the roll information;
the electronic circuit compares eye response in one direction using the eye orientation sensor eye movement information and head orientation information with eye response in the opposite direction using the eye orientation movement information and the head orientation information to determine asymmetry;
the electronic circuit comprises an element that compares a gain signal and a phase signal with a reference value to determine if the measured eye response is normal or abnormal; and
the electronic circuit transmits a signal responsive to the eye orientation sensor to a remote device using a wireless communications interface.

3. The system of claim 2 wherein:
the portable device is a self-contained device;
the portable device comprises eyewear;
the eyewear comprises a lens;
the eye sensor is responsive to a Purkinje image;
the video camera is responsive to infrared light;
the power supply comprises a wireless recharging interface;
the battery comprises a lithium ion battery;
the system comprises a display;
the display comprises a 3-dimensional element;
the display is responsive to the video camera;
the display is responsive to the head movement;
the electronic circuit generates a multi-frequency composite score for a measurement selected from the group consisting of vestibulo-ocular reflex, dynamic visual acuity, dynamic visual stability, and retinal image stability in response to a plurality of signals at a plurality of frequencies selected from the group consisting of a plurality of phase signals, a plurality of gain signals, and a plurality of asymmetry signals;
the memory unit comprises functionality to store a plurality of multi-frequency composite scores whereby the system can be used for data logging;
the wireless communications interface comprises a ZigBee communications protocol;
the system comprises a Global Positioning System receiver;
the system comprises a calibration function; and
the system comprises ocular reflex improvement information for the user.

4. A portable eye response measuring system comprising:
an eye orientation sensor wherein the eye orientation sensor senses movement of at least one eye wherein the eye movement is selected from the group consisting of vertical eye movement and horizontal eye movement;
a head orientation sensor wherein:
  the head orientation sensor is attachable to a person's head;
  the head orientation sensor senses movement of the person's head wherein the head movement is selected from the group consisting of pitch movement and yaw movement; and
  the head orientation sensor senses movement in a range of frequencies that comprises at least one frequency between 0.01 Hertz and 15 Hertz;
  the head orientation sensor comprises a micro-electromechanical system integrated circuit comprising a device selected from the group consisting of an accelerometer, a magnetometer, and a gyroscope; and
an electronic circuit wherein:
  the electronic circuit comprises logic circuitry, a central processing unit, a memory unit; and sensor data pre-processing circuitry;
  the electronic circuit is responsive to the movement information received from the eye orientation sensor;
  the electronic circuit is responsive to the movement information received from the head orientation sensor;

the electronic circuit is configured to transmit, using a communications interface coupled to a remote device, eye movement information and/or head movement information; and the electronic circuit uses a Fourier transform to generate a signal selected from the group consisting of a phase signal and a gain signal in response to eye movement information received from the eye orientation sensor and head movement information received from the head orientation sensor.

5. The system of claim 4 wherein:

the system is designed for use in an ambulatory occupational environment outside of a medical facility;

the system measures a physiological condition selected from the group consisting of vestibulo-ocular reflex, dynamic visual acuity, dynamic visual stability, and retinal image stability;

the eye orientation sensor senses movement of both the left eye and the right eye;

the electronic circuit is responsive to both left eye movement information and right eye movement information received from the eye orientation sensor;

the electronic circuit uses the Fourier transform to generate both a gain signal and a phase signal;

the electronic circuit compares eye response in one direction using the eye orientation sensor eye movement information and head orientation information with eye response in the opposite direction using the eye orientation movement information and the head orientation information to determine asymmetry;

the electronic circuit comprises an element that compares a gain signal and a phase signal with a reference value to determine if the measured eye response is normal or abnormal.

6. The system of claim 4 wherein:

the electronic circuit generates a multi-frequency composite score for a measurement selected from the group consisting of vestibulo-ocular reflex, dynamic visual acuity, dynamic visual stability, and retinal image stability in response to a plurality of signals at a plurality of frequencies selected from the group consisting of a plurality of phase signals, a plurality of gain signals, and a plurality of asymmetry signals.

7. The system of claim 4 wherein:

the eye sensor comprises a mobile electronic device selected from the group consisting of a smart phone, a smart watch, a hand-held electronic device, and a body-attached electronic device.

8. The system of claim 4 wherein:

the eye orientation sensor comprises an image detector;

the image detector comprises a video camera; and the video camera is responsive to infrared light.

9. The system of claim 4 wherein:

the eye orientation sensor comprises a module selected from the group consisting of an image detector, a magnetic field detector, and an electrical potential detector;

the eye orientation sensor senses vertical movement and horizontal movement of at least one eye;

the head orientation sensor senses pitch and yaw of the person's head wherein pitch represents a rotation about a first axis representing up and down movement of the person's face when the rear of the person's head moves in the opposite direction and yaw represents horizontal movement of the face when looked at from the front about a second axis substantially aligned with the spine and perpendicular to the first axis;

the electronic circuit uses a Fourier transform to generate a vertical signal selected from the group consisting of a gain signal and a phase signal in response to the vertical eye movement information and the pitch information; and the electronic circuit uses a Fourier transform to generate a horizontal signal selected from the group consisting of a gain signal and a phase signal in response to the horizontal eye movement information and the yaw information.

10. The system of claim 4 wherein:

the system measures a physiological condition selected from the group consisting of vestibulo-ocular reflex, dynamic visual acuity, dynamic visual stability, and retinal image stability;

the electronic circuit uses a Fourier transform to generate a phase signal and a gain signal in response to eye movement information received from the eye orientation sensor and the head movement information received from the head orientation sensor; and the electronic circuit comprises an element that compares the gain signal and the phase signal with a reference value to determine if the measured eye response is normal or abnormal.

11. The system of claim 4 wherein:

the electronic circuit generates a multi-frequency composite score for a measurement selected from the group consisting of vestibulo-ocular reflex, dynamic visual acuity, dynamic visual stability, and retinal image stability in response to a plurality of signals at a plurality of frequencies selected from the group consisting of a plurality of phase signals, a plurality of gain signals, and a plurality of asymmetry signals; and the memory unit comprises functionality to store a plurality of multi-frequency composite scores whereby the system can be used for data logging.

12. The system of claim 4 wherein:

the system is designed for use in an ambulatory occupational environment outside of a medical facility.

13. The system of claim 4 wherein:

the eye orientation sensor senses movement of both the left eye and the right eye; and the electronic circuit is responsive to both left eye movement information and right eye movement information received from the eye orientation sensor.

14. The system of claim 4 wherein:

the system comprises eyewear; and the eyewear comprises a lens.

15. An eye reflex detection method, the method comprising the steps of:

electronically sensing changes in eye orientation wherein:
the eye orientation changes are sensed by a portable device; and
the eye orientation changes are selected from the group consisting of vertical eye movement and horizontal eye movement;

electronically sensing changes in head orientation wherein:
the head orientation changes are sensed by a portable device;
the head orientation changes are selected from the group consisting of pitch movement and yaw movement;
the head orientation changes are sensed in at least one frequency that is between 0.01 Hertz and 15 Hertz; and head orientation sensing comprises the use of a device selected from the group consisting of an accelerometer, a magnetometer, and a gyroscope;

comparing the eye orientation and head orientation information using an electronic circuit wherein:

the electronic circuit comprises logic circuitry, a central processing unit, a memory unit; and sensor data pre-processing circuitry;

the electronic circuit uses a Fourier transform to generate a signal selected from the group consisting of a phase signal and a gain signal in response to the eye orientation changes and the head orientation changes; and transmitting orientation information from the electronic circuit related to the eye orientation changes and/or head orientation changes.

16. The eye reflex detection method of claim 15 wherein:
the Fourier transform generates a phase signal and a gain signal in response to the eye orientation changes and the head orientation changes;
the method further comprises the step of generating a multi-frequency composite score in response to the signal generated by the Fourier transform.

17. The eye reflex detection method of claim 15 wherein:
sensing eye orientation changes comprises sensing vertical eye movement and horizontal eye movement;
sensing head orientation changes comprises sensing pitch movement and yaw movement; and
the Fourier transform generates a horizontal signal and vertical signal in response to the eye orientation changes and the head orientation changes.

18. The eye reflex detection method of claim 15, further comprising the steps of:
storing multiple readings of the output from the Fourier transform in a data log.

19. The eye reflex detection method of claim 15 wherein:
the method is applied in an ambulatory occupational environment outside of a medical facility; and
the method measures a physiological condition selected from the group consisting of vestibulo-ocular reflex, dynamic visual acuity, dynamic visual stability, and retinal image stability.

* * * * *